US012458460B2

(12) United States Patent
Fischer et al.

(10) Patent No.: US 12,458,460 B2
(45) Date of Patent: Nov. 4, 2025

(54) MAINTAINING CABLE ROUTING IN CABLE-ACTUATED SURGICAL TOOLS

(71) Applicant: Cilag GmbH International, Zug (CH)

(72) Inventors: Austin Michael Fischer, Cincinnati, OH (US); Christopher William Birri, West Chester, OH (US)

(73) Assignee: Cilag GmbH International, Zug (CH)

( * ) Notice: Subject to any disclaimer, the term of this patent is extended or adjusted under 35 U.S.C. 154(b) by 421 days.

(21) Appl. No.: 18/170,329

(22) Filed: Feb. 16, 2023

(65) Prior Publication Data

US 2024/0277436 A1 Aug. 22, 2024

(51) Int. Cl.
*A61B 34/00* (2016.01)
*A61B 34/30* (2016.01)

(52) U.S. Cl.
CPC ........ *A61B 34/71* (2016.02); *A61B 2034/305* (2016.02)

(58) Field of Classification Search
CPC .............. A61B 34/71; A61B 2034/305; A61B 2090/035; A61B 34/30
See application file for complete search history.

(56) References Cited

U.S. PATENT DOCUMENTS

2019/0125465 A1* 5/2019 Evans .................... A61B 34/30
2020/0315728 A1* 10/2020 Johnson ................. A61B 34/71
2022/0202437 A1* 6/2022 Overmyer ........ A61B 17/00234

* cited by examiner

*Primary Examiner* — Carl H Layno
*Assistant Examiner* — Dhrasti Snehal Dalal
(74) *Attorney, Agent, or Firm* — Vorys, Sater, Seymour and Pease LLP

(57) ABSTRACT

A surgical tool includes a drive housing, a drive input rotatably mounted to a bottom of the drive housing, a capstan assembly arranged within the drive housing and operatively coupled to the drive input such that rotation of the drive input correspondingly actuates the capstan assembly, a static actuation limiter arranged within the drive housing, and a dynamic actuation limiter provided by the capstan assembly and engageable with the static actuation limiter as the capstan assembly is actuated. Engaging the dynamic actuation limiter against the static actuation limiter stops actuation of the capstan assembly.

26 Claims, 12 Drawing Sheets

MAINTAINING CABLE ROUTING IN CABLE-ACTUATED SURGICAL TOOLS

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The instruments and tools introduced into the abdominal cavity via the trocar can be used to engage and/or treat tissue in a number of ways to achieve a diagnostic or therapeutic effect.

Various robotic systems have been developed to assist in MIS procedures. Robotic systems can allow for more instinctive hand movements by maintaining natural eye-hand axis. Robotic systems can also allow for more degrees of freedom in movement by including an articulable "wrist" joint that creates a more natural hand-like articulation. In such systems, an end effector positioned at the distal end of the instrument can be articulated (moved) using a cable driven motion system having one or more drive cables that extend through the wrist joint. A user (e.g., a surgeon) is able to remotely operate the end effector by grasping and manipulating in space one or more controllers that communicate with a tool driver coupled to the surgical instrument. User inputs are processed by a computer system incorporated into the robotic surgical system, and the tool driver responds by actuating the cable driven motion system. Moving the drive cables articulates the end effector to desired angular positions and configurations.

Some cable driven motion systems utilize antagonistic cable designs with multiple drive inputs to drive end effector functionality and articulation. Operation of the surgical tool can sometimes introduce slack in the drive cables, which can result in cable derailment or inadvertently feeding the drive cable into intermeshed gears.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to robotic surgical systems and, more particularly, to preventing derailment and binding issues with drive cables of a cable driven surgical tool when slack accumulates in the drive cables.

Embodiments discussed herein describe a surgical tool that includes a drive housing, a drive input rotatably mounted to a bottom of the drive housing, and a capstan assembly arranged within the drive housing and operatively coupled to the drive input such that rotation of the drive input correspondingly actuates the capstan assembly. A static actuation limiter arranged within the drive housing, and a dynamic actuation limiter is provided by the capstan assembly and engageable with the static actuation limiter as the capstan assembly is actuated. Engaging the dynamic actuation limiter against the static actuation limiter stops actuation of the capstan assembly and thereby help mitigate slack events in drive cables.

Embodiments included herein also describe anti-derailment features offset from the outer circumference of a pulley arranged within the drive housing. Such anti-derailment features may help maintain the drive cable within the cable pulley as the cable pulley rotates. Also disclosed herein are standoff features that are arranged to interpose drive cables and a geared interface between a drive gear and a driven gear. Such standoff features may help prevent the drive cable from feeding into the geared interface. The anti-derailment and standoff features may prove advantageous for several reasons. For example, such features help prevent the drive cables from derailing from corresponding idler and cable pulleys that maintain the routing pathway of the drive cables within the drive housing. Moreover, such features allow the drive cables to slack or slacken, but still maintain the same exact routing without derailment until cable tension is resumed. The features also help maintain routing of the drive cable during operation. Furthermore, the anti-derailment and standoff features may be implemented as simple features provided in existing molded components.

Figure 1:
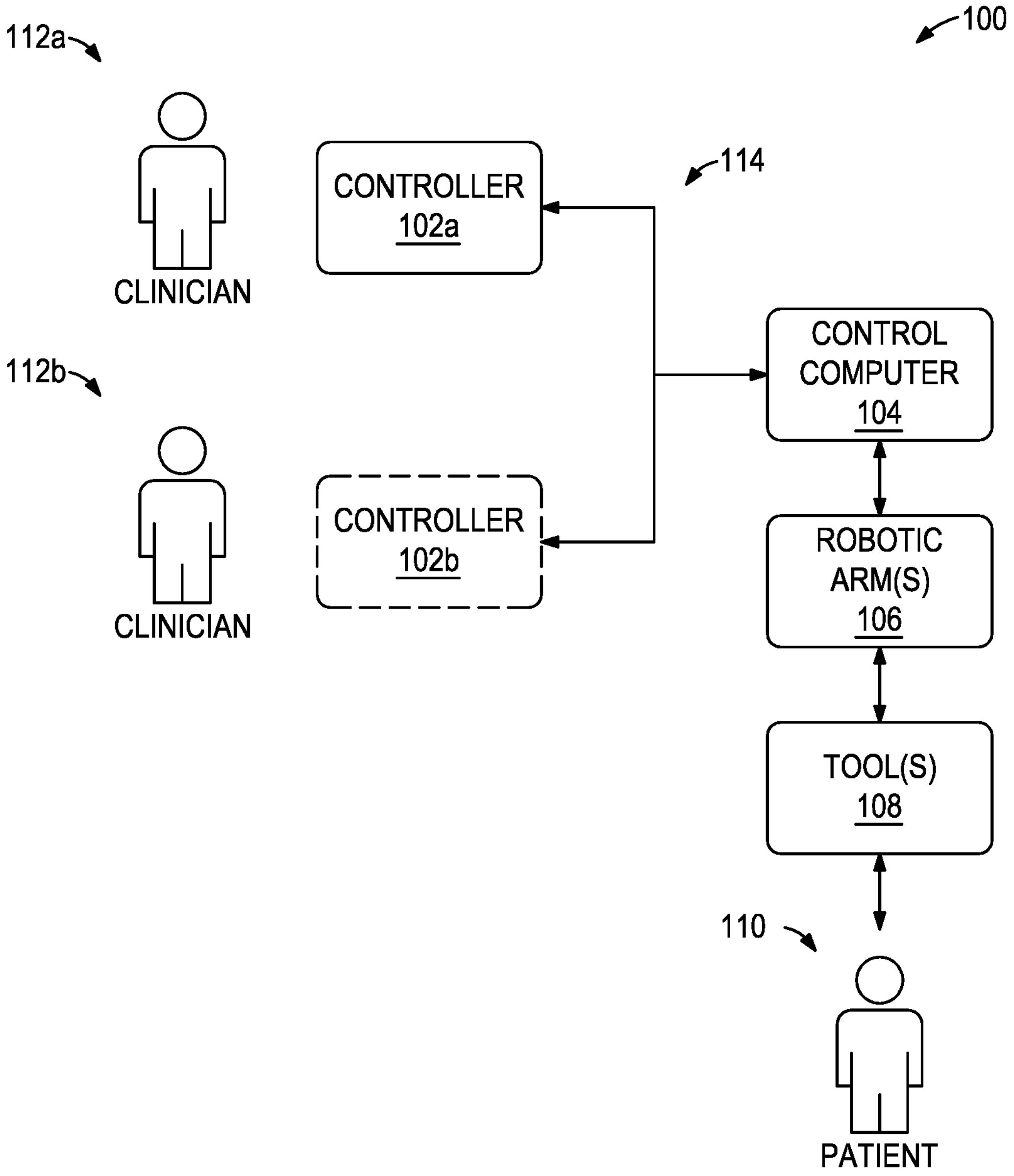
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one set of user input controllers 102*a* and at least one control computer 104. The control computer 104 may be mechanically and/or electrically coupled to a robotic manipulator and, more particularly, to one or more robotic arms 106 (alternately referred to as "tool drivers"). In some embodiments, the robotic manipulator may be included in or otherwise mounted to an arm cart capable of making the system portable. Each robotic arm 106 may include and otherwise provide a location for mounting one or more surgical instruments or tools 108 for performing various surgical tasks on a patient 110. Operation of the robotic arms 106 and associated tools 108 may be directed by a clinician 112*a* (e.g., a surgeon) from the user input controller 102*a*.

In some embodiments, a second set of user input controllers 102*b* (shown in dashed line) may be operated by a second clinician 112*b* to direct operation of the robotic arms 106 and tools 108 via the control computer 104 and in conjunction with the first clinician 112*a*. In such embodiments, for example, each clinician 112*a,b* may control different robotic arms 106 or, in some cases, complete control of the robotic arms 106 may be passed between the clinicians 112*a,b* as needed. In some embodiments, additional robotic manipulators having additional robotic arms may be utilized during surgery on the patient 110, and these additional robotic arms may be controlled by one or more of the user input controllers 102*a,b*.

The control computer 104 and the user input controllers 102*a,b* may be in communication with one another via a communications link 114, which may be any type of wired or wireless telecommunications means configured to carry a variety of communication signals (e.g., electrical, optical, infrared, etc.) according to any communications protocol. In some applications, for example, there is a tower with ancillary equipment and processing cores designed to drive the robotic arms 106.

The user input controllers 102*a,b* generally include one or more physical controllers that can be grasped by the clinicians 112*a,b* and manipulated in space while the surgeon views the procedure via a stereo display. The physical controllers generally comprise manual input devices movable in multiple degrees of freedom, and which often include an actuatable handle for actuating the surgical tool(s) 108, for example, for opening and closing opposing jaws, applying an electrical potential (current) to an electrode, or the like. The control computer 104 can also include an optional feedback meter viewable by the clinicians 112*a,b* via a display to provide a visual indication of various surgical instrument metrics, such as the amount of force being applied to the surgical instrument (i.e., a cutting instrument or dynamic clamping member).

Figures 2, 3:
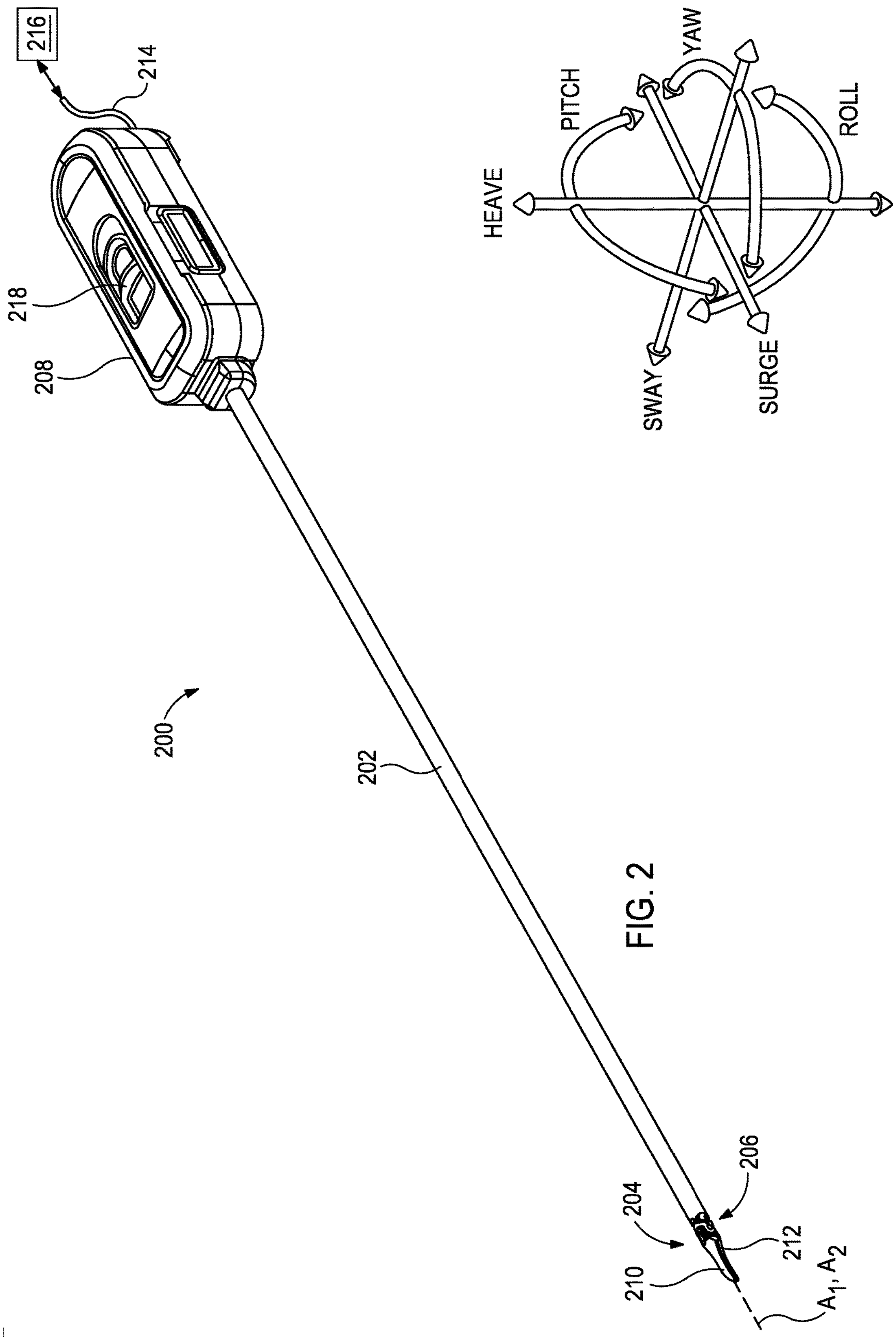
FIG. 2 is an isometric side view of an example surgical tool that may incorporate some or all of the principles of the present disclosure.
FIG. 3 illustrates potential degrees of freedom in which the wrist of the surgical tool of FIG. 2 may be able to articulate (pivot) and translate.

FIG. 2 is an isometric side view of an example surgical tool 200 that may incorporate some or all of the principles of the present disclosure. The surgical tool 200 may be the same as or similar to the surgical tool(s) 108 of FIG. 1 and, therefore, may be used in conjunction with a robotic surgical system, such as the robotic surgical system 100 of FIG. 1. Accordingly, the surgical tool 200 may be designed to be releasably coupled to a tool driver included in the robotic surgical system 100. In other embodiments, however, aspects of the surgical tool 200 may be adapted for use in a manual or hand-operated manner, without departing from the scope of the disclosure.

As illustrated, the surgical tool 200 includes an elongated shaft 202, an end effector 204, a wrist 206 (alternately referred to as a "wrist joint" or an "articulable wrist joint") that couples the end effector 204 to the distal end of the shaft 202, and a drive housing 208 coupled to the proximal end of the shaft 202. In applications where the surgical tool is used in conjunction with a robotic surgical system (e.g., the robotic surgical system 100 of FIG. 1), the drive housing 208 can include coupling features that releasably couple the surgical tool 200 to the robotic surgical system.

The terms "proximal" and "distal" are defined herein relative to a robotic surgical system having an interface configured to mechanically and electrically couple the surgical tool 200 (e.g., the housing 208) to a robotic manipulator. The term "proximal" refers to the position of an element closer to the robotic manipulator and the term "distal" refers to the position of an element closer to the end effector 204 and thus further away from the robotic manipulator. Alternatively, in manual or hand-operated applications, the terms "proximal" and "distal" are defined herein relative to a user, such as a surgeon or clinician. The term "proximal" refers to the position of an element closer to the user and the term "distal" refers to the position of an element closer to the end effector 204 and thus further away from the user. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 200, the end effector 204 is configured to move (pivot) relative to the shaft 202 at the wrist 206 to position the end effector 204 at desired orientations and locations relative to a surgical site. To accomplish this, the housing 208 includes (contains) various drive inputs and mechanisms (e.g., gears, actuators, etc.) designed to control operation of various features associated with the end effector 204 (e.g., clamping, firing, cutting, rotation, articulation, etc.). In at least some embodiments, the shaft 202, and hence the end effector 204 coupled thereto, is configured to rotate about a longitudinal axis $A_1$ of the shaft 202. In such embodiments, at least one of the drive inputs included in the housing 208 is configured to control rotational movement of the shaft 202 about the longitudinal axis $A_1$.

The shaft 202 is an elongate member extending distally from the housing 208 and has at least one lumen extending therethrough along its axial length. In some embodiments, the shaft 202 may be fixed to the housing 208, but could alternatively be rotatably mounted to the housing 208 to allow the shaft 202 to rotate about the longitudinal axis $A_1$. In yet other embodiments, the shaft 202 may be releasably coupled to the housing 208, which may allow a single housing 208 to be adaptable to various shafts having different end effectors.

The end effector 204 can exhibit a variety of sizes, shapes, and configurations. In the illustrated embodiment, the end effector 204 comprises a combination tissue grasper and vessel sealer that include opposing first (upper) and second (lower) jaws 210, 212 configured to move (articulate) between open and closed positions. As will be appreciated, however, the opposing jaws 210, 212 may alternatively form part of other types of end effectors such as, but not limited to, a surgical scissors, a clip applier, a needle driver, a babcock including a pair of opposed grasping jaws, bipolar jaws (e.g., bipolar Maryland grasper, forceps, a fenestrated grasper, etc.), etc. One or both of the jaws 210, 212 may be configured to pivot to articulate the end effector 204 between the open and closed positions.

FIG. 3 illustrates the potential degrees of freedom in which the wrist 206 may be able to articulate (pivot) and thereby move the end effector 204. The wrist 206 can have any of a variety of configurations. In general, the wrist 206 comprises a joint configured to allow pivoting movement of the end effector 204 relative to the shaft 202. The degrees of freedom of the wrist 206 are represented by three translational variables (i.e., surge, heave, and sway), and by three rotational variables (i.e., Euler angles or roll, pitch, and yaw). The translational and rotational variables describe the position and orientation of the end effector 204 with respect to a given reference Cartesian frame. As depicted in FIG. 3, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 206 (e.g., X-axis), yaw movement about a second axis of the wrist 206 (e.g., Y-axis), and combinations thereof to allow for 360° rotational movement of the end effector 204 about the wrist 206. In other applications, the pivoting motion can be limited to movement in a single plane, e.g., only pitch movement about the first axis of the wrist 206 or only yaw movement about the second axis of the wrist 206, such that the end effector 204 moves only in a single plane.

Referring again to FIG. 2, the surgical tool 200 may also include a plurality of drive cables (obscured in FIG. 2) that form part of a cable driven motion system configured to facilitate actuation and articulation of the end effector 204 relative to the shaft 202. Moving (actuating) one or more of the drive cables moves the end effector 204 between an unarticulated position and an articulated position. The end effector 204 is depicted in FIG. 2 in the unarticulated position where a longitudinal axis $A_2$ of the end effector 204 is substantially aligned with the longitudinal axis $A_1$ of the shaft 202, such that the end effector 204 is at a substantially zero angle relative to the shaft 202. Due to factors such as manufacturing tolerance and precision of measurement devices, the end effector 204 may not be at a precise zero angle relative to the shaft 202 in the unarticulated position, but nevertheless be considered "substantially aligned" thereto. In the articulated position, the longitudinal axes $A_1$, $A_2$ would be angularly offset from each other such that the end effector 204 is at a non-zero angle relative to the shaft 202.

In some embodiments, the surgical tool 200 may be supplied with electrical power (current) via a power cable 214 coupled to the housing 208. In other embodiments, the power cable 214 may be omitted and electrical power may be supplied to the surgical tool 200 via an internal power source, such as one or more batteries, capacitors, or fuel cells. In such embodiments, the surgical tool 200 may alternatively be characterized and otherwise referred to as an "electrosurgical instrument" capable of providing electrical energy to the end effector 204.

The power cable 214 may place the surgical tool 200 in electrical communication with a generator 216 that supplies energy, such as electrical energy (e.g., radio frequency energy), ultrasonic energy, microwave energy, heat energy, or any combination thereof, to the surgical tool 200 and, more particularly, to the end effector 204. Accordingly, the generator 216 may comprise a radio frequency (RF) source, an ultrasonic source, a direct current source, and/or any other suitable type of electrical energy source that may be activated independently or simultaneously.

In applications where the surgical tool 200 is configured for bipolar operation, the power cable 214 will include a supply conductor and a return conductor. Current can be supplied from the generator 216 to an active (or source) electrode located at the end effector 204 via the supply conductor, and current can flow back to the generator 216 via a return electrode located at the end effector 204 via the return conductor. In the case of a bipolar grasper with opposing jaws, for example, the jaws serve as the electrodes where the proximal end of the jaws are isolated from one another and the inner surface of the jaws (i.e., the area of the jaws that grasp tissue) apply the current in a controlled path through the tissue. In applications where the surgical tool 200 is configured for monopolar operation, the generator 216 transmits current through a supply conductor to an active electrode located at the end effector 204, and current is returned (dissipated) through a return electrode (e.g., a grounding pad) separately coupled to a patient's body.

The surgical tool 200 may further include a manual release switch 218 that may be manually actuated by a user (e.g., a surgeon) to override the cable driven system and thereby manually articulate or operate the end effector 204. The release switch 218 is movably positioned on the drive housing 208, and a user is able to manually move (slide) the release switch 218 from a disengaged position, as shown, to an engaged position. In the disengaged position, the surgical tool 200 is able to operate as normal. As the release switch 218 moves to the engaged position, however, various internal component parts of the drive housing 208 are simultaneously moved, thereby resulting in the jaws 210, 212 opening, which might prove beneficial for a variety of reasons. In some applications, for example, the release switch 218 may be moved in the event of an electrical disruption that renders the surgical tool 200 inoperable. In such applications, the user would be able to manually open the jaws 210, 212 and thereby release any grasped tissue and remove the surgical tool 200. In other applications, the release switch 218 may be actuated (enabled) to open the jaws 210, 212 in preparation for cleaning and/or sterilization of the surgical tool 200.

Figure 4:
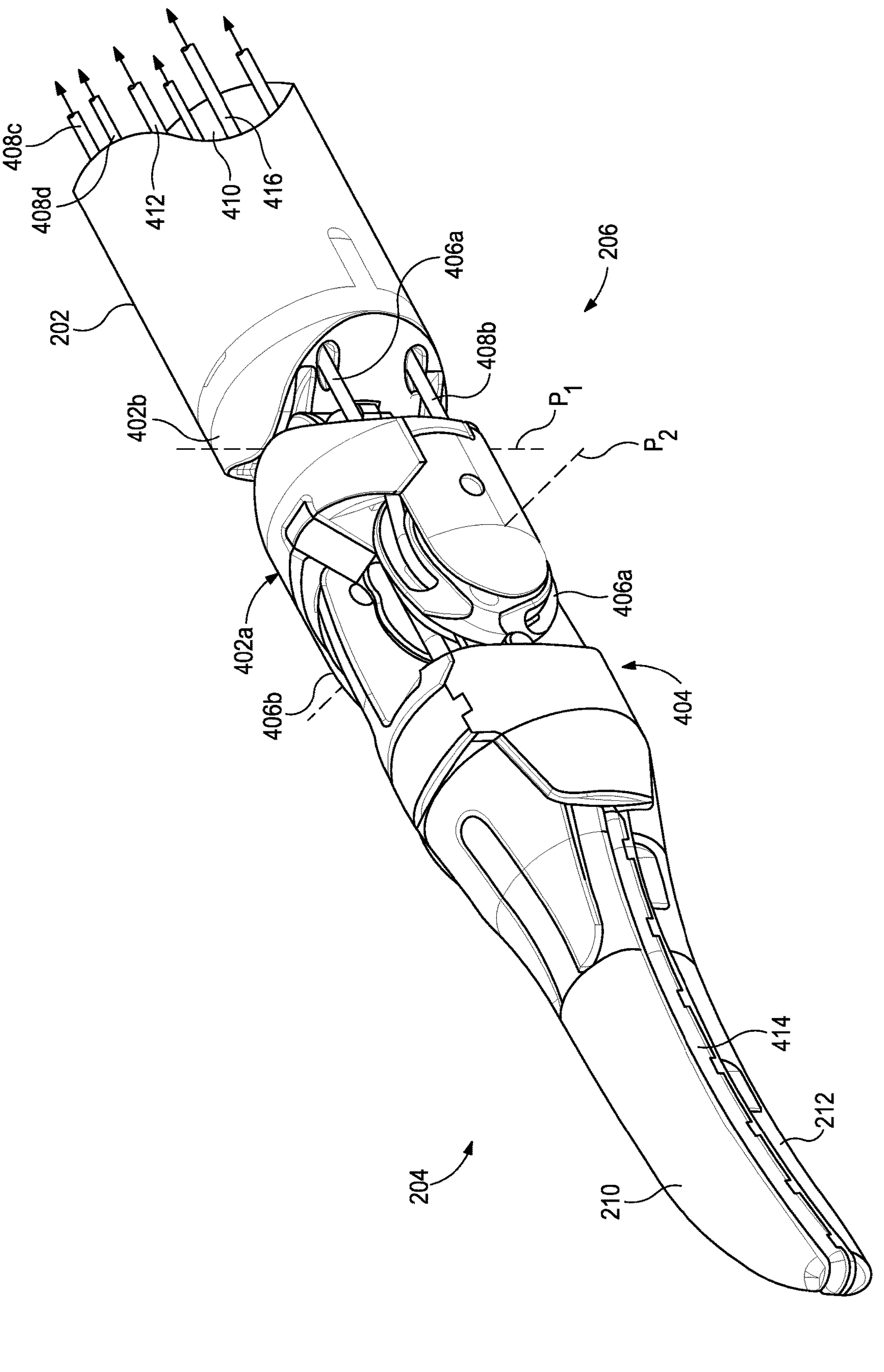
FIG. 4 is an enlarged isometric view of the distal end of the surgical tool of FIG. 2.

FIG. 4 is an enlarged isometric view of the distal end of the surgical tool 200. More specifically, FIG. 4 depicts an enlarged view of the end effector 204 and the wrist 206, with the jaws 210, 212 of the end effector 204 in the closed position. The wrist 206 operatively couples the end effector 204 to the shaft 202. In some embodiments, however, a shaft adapter may be directly coupled to the wrist 206 and otherwise interpose the shaft 202 and the wrist 206. Accordingly, the wrist 206 may be operatively coupled to the shaft 202 either through a direct coupling engagement where the wrist 206 is directly coupled to the distal end of the shaft 202, or an indirect coupling engagement where a shaft adapter interposes the wrist 206 and the distal end of the shaft 202. As used herein, the term "operatively couple" refers to a direct or indirect coupling engagement between two components.

To operatively couple the end effector 204 to the shaft 202, the wrist 206 includes a first or "distal" clevis 402*a* and a second or "proximal" clevis 402*b*. The clevises 402*a,b* are alternatively referred to as "articulation joints" of the wrist 206 and extend from the shaft 202 (or alternatively a shaft adapter). The clevises 402*a,b* are operatively coupled to facilitate articulation of the wrist 206 relative to the shaft 202. As illustrated, the wrist 206 also includes a linkage 404 arranged distal to the distal clevis 402*a* and operatively mounted to the jaws 210, 212.

The proximal end of the distal clevis 402*a* may be rotatably mounted or pivotably coupled to the proximal clevis 402*b* at a first pivot axis $P_1$ of the wrist 206. In some embodiments, an axle may extend through the first pivot axis $P_1$ and the distal and proximal clevises 402*a,b* may be rotatably coupled via the axle. In other embodiments, however, such as is depicted in FIG. 4, the distal and proximal clevises 402*a,b* may be engaged in rolling contact, such as via an intermeshed gear relationship that allows the clevises 402*a,b* to rotate relative to each other similar to a rolling joint.

First and second pulleys 406*a* and 406*b* may be rotatably mounted to the distal end of the distal clevis 402*a* at a second pivot axis $P_2$ of the wrist 206. The linkage 404 may be arranged distal to the second pivot axis $P_2$ and operatively mounted to the jaws 210, 212. The first pivot axis $P_1$ is substantially perpendicular (orthogonal) to the longitudinal axis $A_1$ of the shaft 202, and the second pivot axis $P_2$ is substantially perpendicular (orthogonal) to both the longitudinal axis $A_1$ and the first pivot axis $P_1$. Movement of the end effector 204 about the first pivot axis $P_1$ provides "yaw" articulation of the wrist 206, and movement about the second pivot axis $P_2$ provides "pitch" articulation of the wrist 206.

A plurality of drive cables, shown as drive cables 408*a*, 408*b*, 408*c*, and 408*d*, extend longitudinally within a lumen 410 defined by the shaft 202 (or a shaft adaptor) and extend at least partially through the wrist 206. The drive cables 408*a-d* may form part of the cable driven motion system housed within the drive housing 208 (FIG. 2), and may comprise cables, bands, lines, cords, wires, woven wires, ropes, strings, twisted strings, elongate members, belts, shafts, flexible shafts, drive rods, or any combination thereof. The drive cables 408*a-d* can be made from a variety of materials including, but not limited to, a metal (e.g., tungsten, stainless steel, nitinol, etc.), a polymer (e.g., ultra-high molecular weight polyethylene), a synthetic fiber (e.g., KEVLAR®, VECTRAN®, etc.), an elastomer, or any combination thereof. While four drive cables 408*a-d* are depicted in FIG. 4, more or less than four may be employed, without departing from the scope of the disclosure.

The drive cables 408*a-d* extend proximally from the end effector 204 and the wrist 206 toward the drive housing 208 (FIG. 2) where they are operatively coupled to various actuation mechanisms or devices that facilitate longitudinal movement (translation) of the drive cables 408*a-d* within the lumen 410. Selective actuation of the drive cables 408*a-d* applies tension (i.e., pull force) to the given drive cable 408*a-d* in the proximal direction, which urges the given drive cable 408*a-d* to translate longitudinally within the lumen 410.

In the illustrated embodiment, the drive cables 408*a-d* each extend longitudinally through the proximal clevis 402*b*. The distal end of each drive cable 408*a-d* terminates at the first or second pulleys 406*a,b*, thus operatively coupling each drive cable 408*a-d* to the end effector 204. In some embodiments, the distal ends of the first and second drive cables 408*a,b* may be coupled to each other and terminate at the first pulley 406*a*, and the distal ends of the third and fourth drive cables 408*c,d* may be coupled to each other and terminate at the second pulley 406*b*. In at least one embodiment, the distal ends of the first and second drive cables 408*a,b* and the distal ends of the third and fourth drive cables 408*c,d* may each be coupled together at corresponding ball crimps (not shown) mounted to the first and second pulleys 406*a,b*, respectively.

In at least one embodiment, the drive cables 408*a-d* may operate "antagonistically". More specifically, when the first drive cable 408*a* is actuated (moved), the second drive cable 408*b* naturally follows as coupled to the first drive cable 408*a*, and when the third drive cable 408*c* is actuated, the fourth drive cable 408*d* naturally follows as coupled to the third drive cable 408*c*, and vice versa. Antagonistic operation of the drive cables 408*a-d* can open or close the jaws 210, 212. More specifically, selective actuation of the drive cables 408*a-d* in other known configurations or coordination will cause the jaws 210, 212 to open or close. Antagonistic operation of the drive cables 408*a-d* can further cause the end effector 204 to articulate at the wrist 206. More specifically, selective actuation of the drive cables 408*a-d* in known configurations or coordination can cause the end effector 204 to articulate about one or both of the pivot axes $P_1$, $P_2$, thus facilitating articulation of the end effector 204 in both pitch and yaw directions, either individually or simultaneously. Antagonistic operation of the drive cables 408*a-d* advantageously reduces the number of cables required to provide full wrist 206 motion, and also helps eliminate slack in the drive cables 408*a-d*, which results in more precise motion of the end effector 204.

In the illustrated embodiment, the end effector 204 is able to articulate (move) in pitch about the second or "pitch" pivot axis $P_2$, which is located near the distal end of the wrist 206. Thus, the jaws 210, 212 open and close in the direction of pitch. In other embodiments, however, the wrist 206 may alternatively be configured such that the second pivot axis $P_2$ facilitates yaw articulation of the jaws 210, 212, without departing from the scope of the disclosure.

In some embodiments, an electrical conductor 412 may also extend longitudinally within the lumen 410, through the wrist 206, and terminate at an electrode 414 to supply electrical energy to the end effector 204. In some embodiments, the electrical conductor 412 may comprise a wire, but may alternatively comprise a rigid or semi-rigid shaft, rod, or strip (ribbon) made of a conductive material. The electrical conductor 412 may be entirely or partially covered with an insulative covering (overmold) made of a non-conductive material. Using the electrical conductor 412 and the electrode 414, the end effector 204 may be configured for monopolar or bipolar RF operation.

In the illustrated embodiment, the end effector 204 comprises a combination tissue grasper and vessel sealer that includes a knife (not visible), alternately referred to as a "cutting element" or "blade." The knife is aligned with and configured to traverse a guide track (not visible) defined longitudinally in one or both of the upper and lower jaws 210, 212. The knife may be operatively coupled to the distal end of a drive rod 416 that extends longitudinally within the lumen 410 and passes through the wrist 206. Longitudinal movement (translation) of the drive rod 416 correspondingly moves the knife within the guide track(s). Similar to the drive cables 408*a-d*, the drive rod 416 may form part of the actuation systems housed within the drive housing 208 (FIG. 2). Selective actuation of a corresponding drive input will cause the drive rod 416 to move distally or proximally within the lumen 410, and correspondingly move the knife 416 in the same longitudinal direction.

Figure 5:
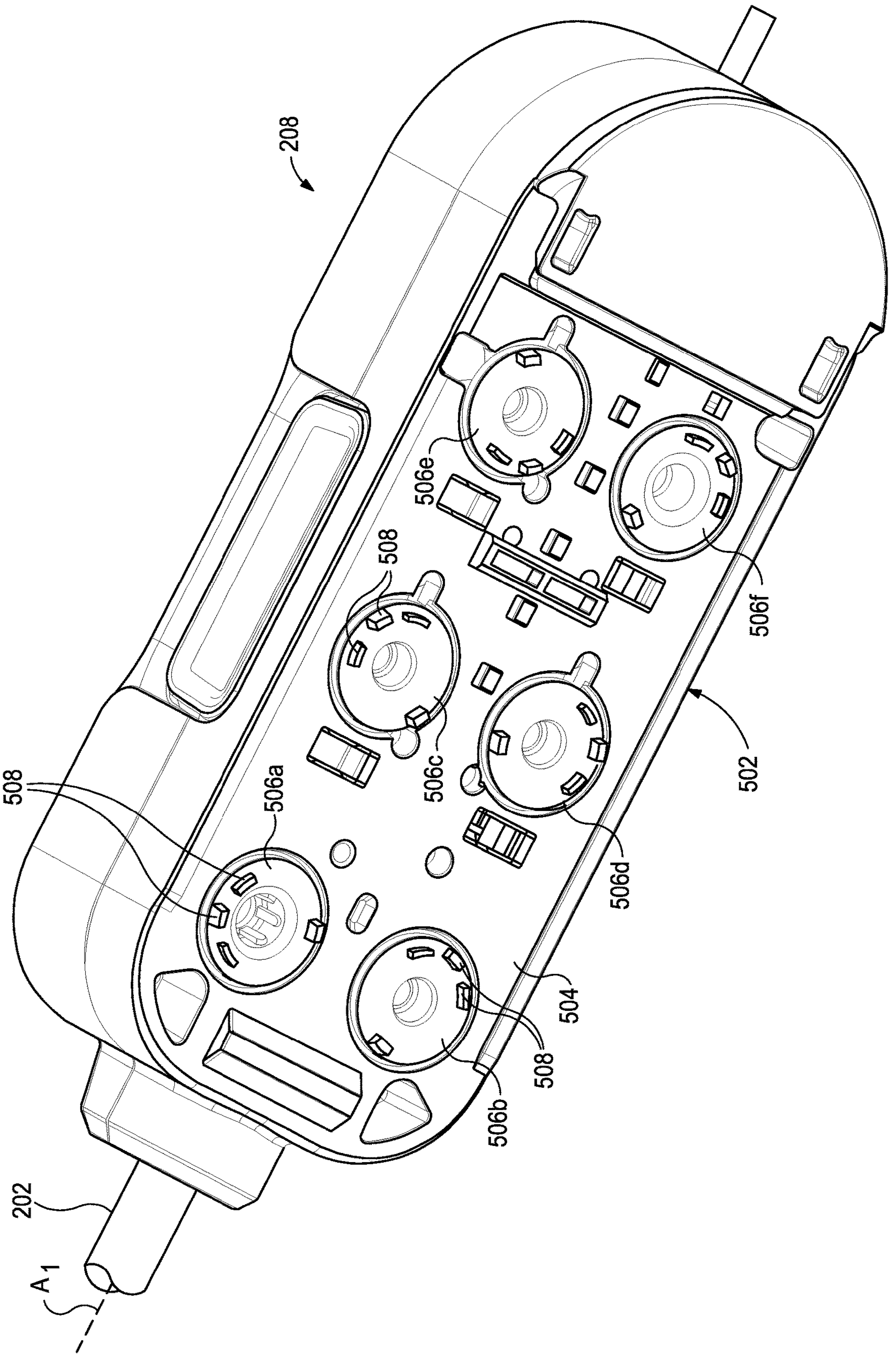
FIG. 5 is a bottom view of the drive housing of FIG. 2, according to one or more embodiments.

FIG. 5 is a bottom view of the drive housing 208, according to one or more embodiments. As illustrated, the drive housing 208 may include a tool mounting portion 502 used to operatively couple the drive housing 208 to a tool driver of a robotic manipulator. The tool mounting portion 502 may releasably couple the drive housing 208 to a tool driver in a variety of ways, such as by clamping thereto, dipping thereto, or slidably mating therewith. In some embodiments, the tool mounting portion 502 may include an array of electrical connecting pins, which may be coupled to an electrical connection on the mounting surface of the tool driver. While the tool mounting portion 502 is described herein with reference to mechanical, electrical, and magnetic coupling elements, it should be understood that a wide variety of telemetry modalities might be used, including infrared, inductive coupling, or the like.

The tool mounting portion 502 includes and otherwise provides an interface 504 configured to mechanically, magnetically, and/or electrically couple the drive housing 208 to the tool driver. As illustrated, the interface 504 includes and supports a plurality of drive inputs, shown as drive inputs 506*a*, 506*b*, 506*c*, 506*d*, 506*e*, and 506*f*. Each drive input 506*a-f* comprises a rotatable disc configured to align with and couple to a corresponding actuator or "drive output" of a tool driver, such that rotation (actuation) of a given drive output drives (rotates) a corresponding one of the drive inputs 506*a-f*. Each drive input 506*a-f* may provide or define one or more surface features 508 configured to align with mating surface features provided on the corresponding drive output. The surface features 508 can include, for example, various protrusions and/or indentations that facilitate a mating engagement. In some embodiments, some or all of the drive inputs 506*a-f* may include one surface feature 508 that is positioned closer to an axis of rotation of the associated drive input 506*a-f* than the other surface feature(s) 508. This may help to ensure positive angular alignment of each drive input 506*a-f*.

In some embodiments, actuation of the first drive input 506*a* may be configured to control rotation of the shaft 202 about its longitudinal axis $A_1$. The shaft 202 may be rotated clockwise or counter-clockwise depending on the rotational actuation of the first drive input 506*a*. In some embodiments, actuation of the second, third, fourth, and fifth drive inputs 506*b-e* may be configured to operate movement (axial translation) of the drive cables 408*a-d* (FIG. 4), which results in the actuation of the wrist 106 (FIG. 4) and/or articulation (operation) of the end effector 204 (FIG. 4). In some embodiments, actuation of the sixth drive input 506*f* may be configured to advance and retract the drive rod 416 (FIG. 4), and thereby correspondingly advance or retract the knife at the end effector 204. Each of the drive inputs 506*a-f* may be actuated based on user inputs communicated to the tool driver coupled to the interface 504, and the user inputs may be received via a computer system incorporated into the robotic surgical system.

Figure 6:
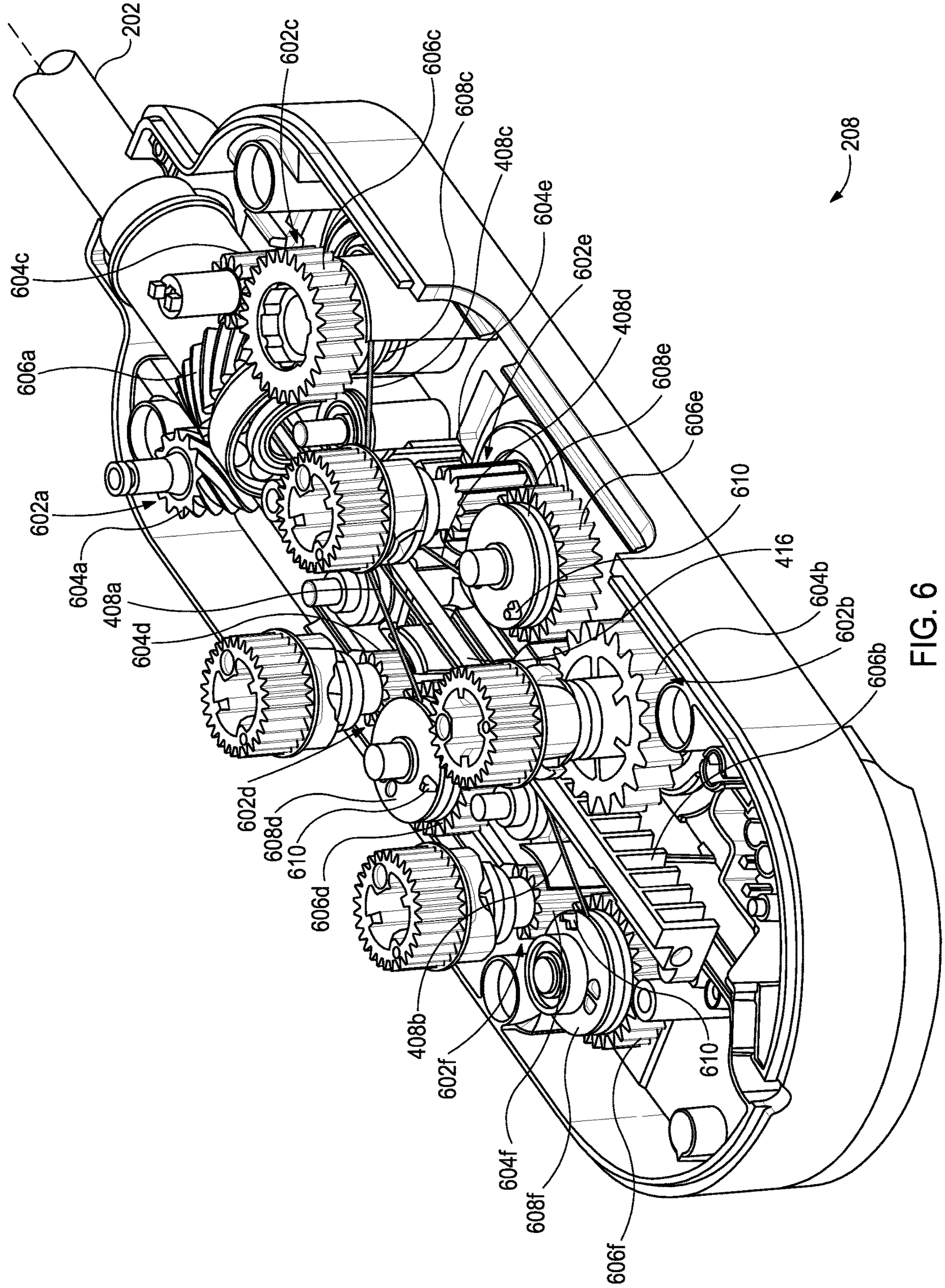
FIG. 6 is an exposed isometric view of the interior of the drive housing of FIG. 2, according to one or more embodiments.

FIG. 6 is an exposed isometric view of the interior of the drive housing 208, according to one or more embodiments. Several component parts that may be otherwise contained within the drive housing 208 are not shown in FIG. 6 to enable discussion of the depicted component parts. As illustrated, the drive housing 208 houses and otherwise contains a plurality of capstan assemblies operable to operate surgical tool 200 (FIG. 2). In particular, a first capstan assembly 602*a* is contained (housed) within the drive housing 208. As illustrated, the first capstan assembly 602*a* may include a drive gear 604*a*, which may be operatively coupled to or extend from the first drive input 506*a* (FIG. 5) such that actuation of the first drive input 506*a* results in rotation of the drive gear 604*a*. In the illustrated embodiment, the drive gear 604*a* comprises a worm gear, which may be configured to mesh and interact with a driven gear 606*a* secured within the drive housing 208 and operatively coupled to the shaft 202 such that rotation of the driven gear 606*a* correspondingly rotates the shaft 202. Accordingly, actuation of the first capstan assembly 602*a*, via actuation of the first drive input 506*a*, will drive the driven gear 606*a* and thereby control rotation of the elongate shaft 202 about the longitudinal axis $A_1$.

The drive housing 208 may further contain or house a second capstan assembly 602*b*, which may include a drive gear 604*b* operatively coupled to or extending from the sixth drive input 506*f* (FIG. 5) such that actuation of the sixth drive input 506*f* results in rotation of the drive gear 604*b*. The drive gear 604*b* is arranged to intermesh with a driven gear 606*b* positioned within the drive housing 208. In the illustrated embodiment, the driven gear 606*b* comprises a rack gear longitudinally translatable within the drive housing 208 as acted upon by the drive gear 604*b*. The drive rod 416 may be operatively coupled to the driven gear 606*b* and extend distally therefrom to the end effector 204 (FIGS. 2 and 4). Accordingly, actuation of the second capstan assembly 602*b*, via actuation of the sixth drive input 506*f*, will cause the driven gear 606*b* to longitudinally translate and correspondingly advance or retract the drive rod 416 and the knife coupled to the end of the drive rod 416 at the end effector 204.

The drive housing 208 further contains or houses third, fourth, fifth, and sixth capstan assemblies 602*c*, 602*d*, 602*e*, and 602*f*, alternately be referred to as "drive cable" capstan assemblies since they are operable to actuate the drive cables 408*a-d*, as described below. While four "drive cable" capstan assemblies 602*c-f* are depicted in FIG. 6, alternative embodiments may include more or less than four, depending on how many drive cables 408*a-d* are used.

In the illustrated embodiment, the third capstan assembly 602*c* is actuated through operation (rotation) of the second drive input 506*b* (FIG. 5), the fourth capstan assembly 602*d* is actuated through operation (rotation) of the third drive input 506*c* (FIG. 5), the fifth capstan assembly 602*e* is actuated through operation (rotation) of the fourth drive input 506*d* (FIG. 5), and the sixth capstan assembly 602*f* is actuated through operation (rotation) of the fifth drive input 506*e* (FIG. 5). As illustrated, each capstan assembly 602*c-f* includes a drive gear 604*c*, 604*d*, 604*e*, and 604*f* that is coupled to or extends from the corresponding drive input 506*b-e*, respectively, such that actuation (rotation) of the drive input 506*b-e* correspondingly rotates the associated drive gear 604*c-f*, respectively.

Moreover, each drive gear 604*c-f* is positioned to mesh and interact with a corresponding driven gear 606*c*, 606*d*, 606*e*, and 606*f* rotatably mounted within the drive housing 208. Each driven gear 606*c-f* includes or is otherwise coupled to a corresponding cable pulley 608*c*, 608*d*, 608*e*, and 608*f*, and each cable pulley 608*c-f* is configured to be operatively coupled to (e.g., has wrapped there around, at least partially) a corresponding one of the drive cables 408*a-d*. In the illustrated embodiment, the first drive cable 408*a* terminates at cable pulley 608*d* ultimately driven by actuation of the fourth capstan assembly 602*d*, the second drive cable 408*b* terminates at cable pulley 608*f* ultimately driven by actuation of the sixth capstan assembly 602*f*, the third drive cable 408*c* terminates at cable pulley 608*c* ultimately driven by actuation of the third capstan assembly 602*c*, and the fourth drive cable 408*d* terminates at cable pulley 608*e* ultimately driven by actuation of the fifth capstan assembly 602*e*.

Accordingly, actuation of the fourth capstan assembly 602*d* (via operation of the third drive input 506*c* of FIG. 5)

will correspondingly control movement of the first drive cable 408*a*; actuation of the sixth capstan assembly 602*f* (via operation of the fifth drive input 506*e* of FIG. 5) will correspondingly control movement of the second drive cable 408*b*; actuation of the third capstan assembly 602*c* (via operation of the second drive input 506*b* of FIG. 5) will correspondingly control movement of the third drive cable 408*c*; and actuation of the fifth capstan assembly 602*e* (via operation of the fourth drive input 506*d* of FIG. 5) will correspondingly control movement of the fourth drive cable 408*d*.

Actuation Limiters to Prevent Incorrect or Excessive Drive Actuation

Still referring to FIG. 6, an antagonistic architecture for the drive cables 408*a-d* enables the amount of tension in each drive cable 408*a-d* to be changed, which helps accurately control operation and actuation of the end effector 204 (FIGS. 2 and 4). Antagonistic architecture also has the drawback or tendency of allowing slack in a single or multiple cables 408*a-d*. If a given drive input 506*b-e* (FIG. 5) is driven excessively in the slack direction, there is a risk that slack may accumulate in the corresponding drive cable 408*a-d*, which may result in the drive cable 408*a-d* derailing from the corresponding cable pulley 608*c-f*. If the drive cable 408*a-d* derails from its corresponding cable pulley 608*c-f*, the surgical tool 200 (FIG. 2) effectively becomes unusable. Moreover, besides risking the accumulation of slack in the corresponding drive cable 408*a-d*, the drive cable 408*a-d* could also fully unwrap from the corresponding cable pulley 608*c-f*. In such a scenario, the ball crimp (not shown) that attaches the drive cable 408*a-d* to the corresponding capstan assembly 602*d-f* could potentially release from the cable pulley 608*d-f*. This would also result in complete device failure of the surgical tool 200.

According to one or more embodiments of the present disclosure, excessive slackening and derailment of the drive cables 408*a-d* from the corresponding cable pulleys 608*c-f* may be mitigated and otherwise entirely prevented by including a dynamic actuation limiter 610 on one or more of the capstan assemblies 602*c-f*. More specifically, in the illustrated embodiment, a dynamic actuation limiter 610 is provided and otherwise defined on the driven gear 606*d-f* of each of the fourth, fifth, and sixth capstan assemblies 602*d-f*. Even more particularly, the dynamic actuation limiter 610 is provided and otherwise defined on the corresponding cable pulley 608*d-f* of the fourth, fifth, and sixth capstan assemblies 602*d-f*. While not shown in FIG. 6, the third capstan assembly 602*c* may also include a dynamic actuation limiter, which may be the same as or similar to the dynamic actuation limiter 610 and serves the same purpose.

In the illustrated embodiment, each dynamic actuation limiter 610 is depicted as a protrusion, a tab, or a boss coupled to and extending from the upper surface of the corresponding cable pulley 608*d-f*. In other embodiments, the dynamic actuation limiter 610 may be provided on and otherwise extend from one or more of the driven gears 608*d-f*. In yet other embodiments, as discussed below, it is contemplated herein to provide the dynamic actuation limiter 610 on one or more of the drive gears 604*d-f*, without departing from the scope of the disclosure. Providing the dynamic actuation limiter 610 on the driven gear 608*d-f* or the drive gear 604*d-f* may have certain advantages. For example, gearing up or down between the driving and driven gears 604*d-f*, 608*d-f* can result in various output differences. Consequently, including the dynamic actuation limiter 610 on the portion of the capstan assembly 602*d-f* that has the highest angular resolution may be advantageous. Moreover, it may be advantageous to provide the dynamic actuation limiter 610 on a portion of the capstan assembly 602*d-f* where it will see lowest amount of load and/or torque. It may also be advantageous to place the dynamic actuation limiter 610 in a region where increased limiter strength is achievable.

Each dynamic actuation limiter 610 may be configured and positioned to interface with a static actuation limiter (not shown) provided and otherwise defined on the drive housing 208. More specifically, as the capstan assembly 602*d-f* is actuated, the corresponding dynamic actuation limiter 610 will also be moved (e.g., rotated). The dynamic actuation limiter 610 is able to be moved (rotated) until engaging a corresponding static actuation limiter provided on the drive housing 208, at which point actuation of the corresponding capstan assembly 602*d*-f is stopped and prevented from further actuation (rotation). The static actuation limiter may be provided at a predetermined angular location that stops the capstan assemblies 602*d-f* from over actuation (rotation), which helps mitigate the accumulation of slack in the corresponding drive cables 408*a-d* and also helps prevent potential derailment of the drive cables 408*a-d*.

Figure 7:
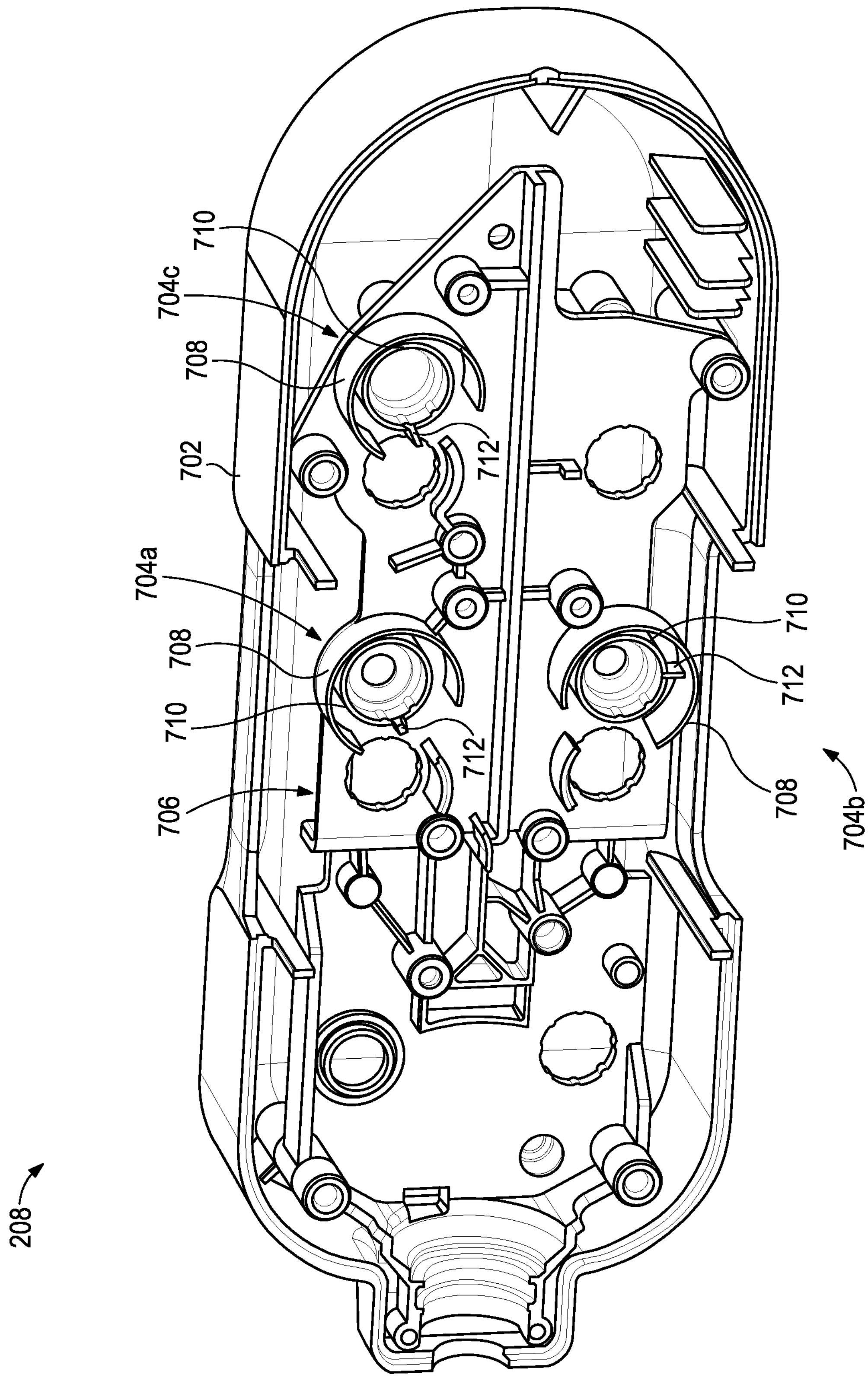
FIG. 7 is an isometric view of the interior of the drive housing of FIG. 2, according to one or more embodiments.

FIG. 7 is an isometric view of the interior of the drive housing 208, according to one or more embodiments. More specifically, FIG. 7 depicts the interior of a first or "upper" portion 702 of the drive housing 208, which may be configured to be operatively coupled to a second or "lower" portion (not shown) of the drive housing 208. Mating the upper portion 702 to the lower portion will form the outer shell and structure of the drive housing 208.

As illustrated, the drive housing 208 may provide and otherwise define a plurality of capstan receptors 704*a*, 704*b*, and 704*c*. In some embodiments, the capstan receptors 704*a-c* may be provided directly on the interior of the upper portion 702 of the drive housing 208. In other embodiments, however, the capstan receptors 704*a-c* may be defined on and otherwise provided by a chassis 706 that may be secured to the interior of the upper portion 702. In yet other embodiments, the capstan receptors 704*a-c* may be provided on the interior of a lower portion (not shown) of the drive housing 208, or on the chassis 706 in an embodiment where the chassis 706 is secured to the interior of the lower portion.

Each capstan receptor 704*a-c* may be configured to align with and receive a portion of a corresponding one of the capstan assemblies 602*d-f* (FIG. 6) when the upper portion 702 is coupled to the lower portion of the drive housing 208. More specifically, the first capstan receptor 704*a* may be configured to receive a portion of the fourth capstan assembly 602*d*, the second capstan receptor 704*b* may be configured to receive a portion of the fifth capstan assembly 602*e*, and the third capstan receptor 704*c* may be configured to receive a portion of the sixth capstan assembly 602*f*. Even more specifically, when the upper portion 702 is coupled to the lower portion of the drive housing 208, the cable pulley 608*d* (FIG. 6) may be received by the first capstan receptor 704*a*, the cable pulley 608*e* (FIG. 6) may be received by the second capstan receptor 704*b*, and the cable pulley 608*f* (FIG. 6) may be received by the third capstan receptor 704*c*. Accordingly, the capstan receptors 704*a-c* may alternately be referred to as "cable pulley" receptors.

In the illustrated embodiment, each capstan receptor 704*a-c* provides and otherwise defines an outer ring 708 and an inner ring 710 concentrically arranged within the outer ring 708. When the upper portion 702 is coupled to the lower portion of the drive housing 208, the outer ring 708 may be configured to receive and extend about the outer circumference of a corresponding cable pulley 608*d-f*, and the inner ring 710 may be configured to receive and extend about a bearing (not shown) rotatably mounted to the cable pulley 608*d-f*. In some embodiments, as illustrated the outer ring 708 may not form a full annular structure. Rather, the outer ring 708 may provide an opening or arcuate cutout, which allows corresponding drive cables 408*a-d* to be received by the associated cable pulley 608*d-f*.

While FIG. 7 depicts the capstan receptors 704*a-c* with specific architecture that includes the outer and inner rings 708, 710, those skilled in the art will readily appreciate that the capstan receptors 704*a-c* may alternatively exhibit other geometries and configurations, without departing from the scope of the disclosure.

As illustrated, each capstan receptor 704*a-c* may provide or otherwise define a corresponding static actuation limiter 712. In the illustrated embodiment, each static actuation limiter 712 is coupled to and otherwise extends from the inner ring 710 of the corresponding capstan receptor 704*a-c*. In other embodiments, however the static actuation limiter 712 may alternatively extend from the outer ring 708, or both. In yet other embodiments, the static actuation limiter 712 may extend from other portions of the drive housing 208 or the chassis 706, without departing from the scope of the disclosure.

Each static actuation limiter 712 may be arranged to interact with a corresponding dynamic actuation limiter 610 (FIG. 6) provided by the corresponding capstan assembly 602*d-f* (FIG. 6). More specifically, and as briefly mentioned above, as the capstan assembly 602*d-f* is actuated, the corresponding dynamic actuation limiter 610 will also be moved (e.g., rotated) until engaging the static actuation limiter 712, which is provided at a predetermined angular location that stops further movement of the capstan assembly 602*d-f*, and thereby prevents over actuation (rotation). Stopping the capstan assemblies 602*d-f* from over actuation (rotation) helps mitigate the accumulation of slack in the corresponding drive cables 408*a-d* (FIG. 6) and also helps prevent potential derailment of the drive cables 408*a-d*.

Figure 8:
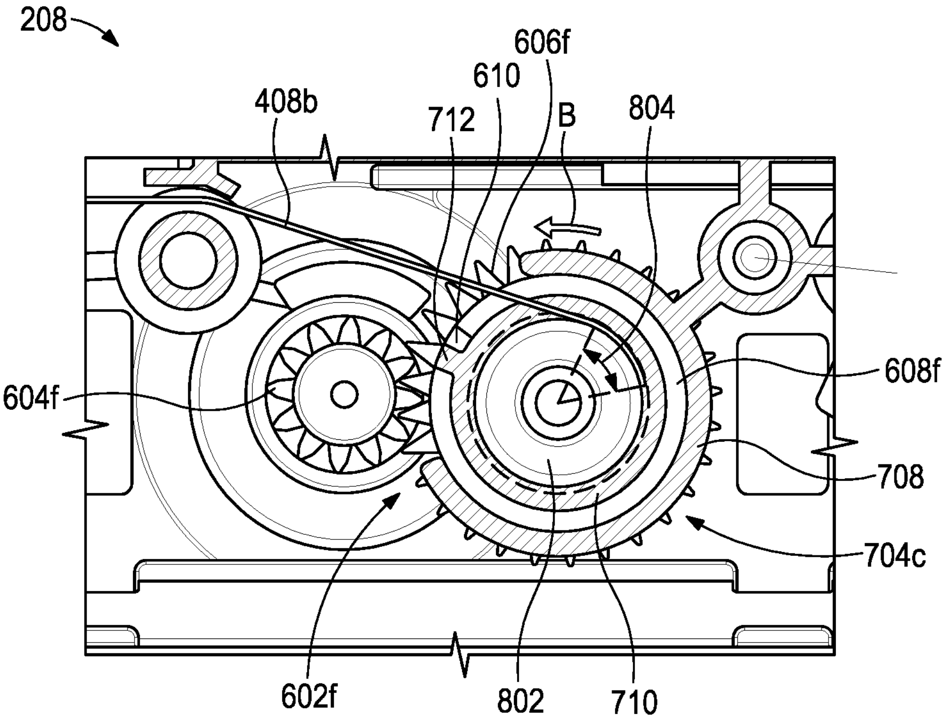
FIG. 8 is a partial cross-sectional top view of a portion of the interior the drive housing of FIG. 2, according to one or more embodiments

FIG. 8 is a partial cross-sectional top view of a portion of the interior the drive housing 208, according to one or more embodiments. More specifically, FIG. 8 is a plan view of the sixth capstan assembly 602*f* received within the third capstan receptor 704*c*. While FIG. 8 depicts the sixth capstan assembly 602*f* received within the third capstan receptor 704*c*, the following discussion is equally applicable to the other capstan assemblies 602*d,e* as received within the corresponding capstan receptors 704*a,b*, respectively.

As illustrated, the second drive cable 408*b* extends to and is at least partially wrapped about the cable pulley 608*f*. The outer ring 708 of the third capstan receptor 704*c* receives and otherwise extends about the outer circumference of the cable pulley 608*f*, which forms part of or otherwise extends from the driven gear 606*f*. As will be described in more detail below, the outer ring 708 may help retain the second drive cable 408*b* within the cable pulley 608*f* as an "anti-derailment feature." Moreover, the inner ring 710 of the third capstan receptor 704*c* receives and extends about a bearing 802 rotatably mounted to the cable pulley 608*f*. In the illustrated embodiment, the static actuation limiter 712 of the third capstan receptor 704*c* extends from the outer circumference of the inner ring 710. As mentioned above, however, the static actuation limiter 712 could alternatively extend from the outer ring 708, without departing from the scope of the disclosure.

Actuating the sixth capstan assembly 602*f* causes the drive gear 604*f* to drive against the driven gear 606*f*, which correspondingly causes the cable pulley 608*f* to rotate either clockwise or counter-clockwise, depending on the angular direction of the drive gear 604*f*. As the cable pulley 608*f* moves (rotates), the dynamic actuation limiter 610 is also moved (e.g., rotated) in the same angular direction. When the cable pulley 608*f* is moved in the counter-clockwise direction, as shown by the arrow B, the second drive cable 408*b* is being "paid out" from the cable pulley 608*f*. The cable pulley 608*f* is able to be moved (rotated) until the dynamic actuation limiter 610 rotates into lateral engagement with the static actuation limiter 712. The static actuation limiter 712 is provided at a predetermined angular location to stop rotation of the cable pulley 608*f* and thereby prevent the sixth capstan assembly 602*f* from over actuation (rotation), which could result in slack in the second drive cable 408*b* or possible derailment of the second drive cable 408*b* from the cable pulley 608*f*.

In the illustrated embodiment, the static actuation limiter 712 may be arranged at a location such that a minimum angular magnitude 804 of the second drive cable 408B remains wrapped about the cable pulley 608*f*. In the illustrated embodiment, the minimum angular magnitude 804 is at least 15°, but could be more or less than 15° without departing from the scope of the disclosure. Accordingly, the sixth capstan assembly 602*f* will be stopped from over actuation (rotation) while at least 15° of the second drive cable 408*b* remains wrapped about the cable pulley 608*f*. As indicated above, this may help mitigate the accumulation of slack in the second drive cable 408*b* and may also help prevent potential derailment of the second drive cable 408*b*.

Figure 9A:
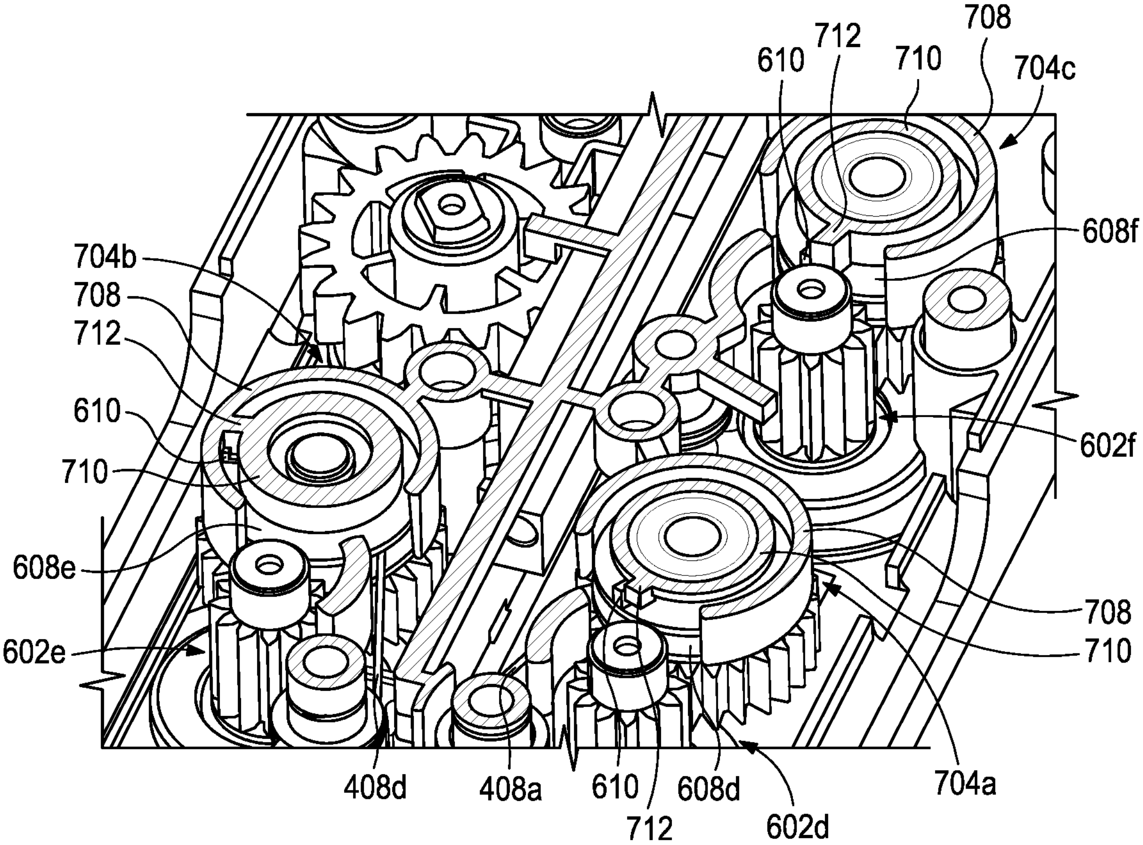
FIG. 9A is an isometric, partial cross-sectional view of a portion of the interior the drive housing of FIG. 2, according to one or more additional embodiments.

FIG. 9A is an isometric, partial cross-sectional view of a portion of the interior the drive housing 208, according to one or more additional embodiments. More specifically, FIG. 9 is an isometric view of the fourth, fifth, and sixth capstan assemblies 602*d-f* received by the first, second, and third capstan receptors 704*a-c*, respectively. As illustrated, the first drive cable 408*a* extends to and is at least partially wrapped about the cable pulley 608*d*, and the fourth drive cable 408*d* extends to and is at least partially wrapped about the cable pulley 608*b*. The second drive cable 408*b* is not visible in FIG. 9, but extends to and is at least partially wrapped about the cable pulley 608*f*.

Each capstan receptor 704*a-c* includes the outer and inner rings 708, 710. The static actuation limiter 712 of the first and third capstan receptors 704*a,c* extends from the outer circumference of the inner ring 710, while the static actuation limiter 12 of the second capstan receptor 704*b* is connected to and extends between the outer and inner rings 708, 710. Moreover, the dynamic actuation limiter 610 of each capstan assembly 602*d-f* extends from the corresponding cable pulley 608*d-f*, but could alternatively extend from other portions of the capstan assembly 602*d-f*, as mentioned above. As each capstan assembly 602*d-f* is actuated, the corresponding dynamic actuation limiter 610 will also be moved (e.g., rotated) and will stop actuation of the corresponding capstan assembly 602*d-f* upon engaging the associated static actuation limiter 712, which is provided at a predetermined angular location that stops the capstan assemblies 602*d-f* from over actuation (rotation). Stopping the capstan assemblies 602*d-f* from over actuation (rotation) helps mitigate the accumulation of slack in the corresponding drive cables 408*a-d* and also helps prevent potential derailment of the drive cables 408*a-d*.

During normal operation, the dynamic actuation limiter 610 will typically not engage the corresponding static actuation limiters 712. However, in the event a given capstan assembly 602*d-f* is directed to be over actuated (or over-rotated), interaction between the dynamic actuation limiters 610 and the corresponding static actuation limiters 712 will ensure that the drive cables 408*a,b,d* remain connected to the corresponding capstan assemblies 602*d-f* and do not unwrap (come undone) during a slack scenario by excessive pay-out. In some embodiments, interaction between the dynamic actuation limiters 610 and the corresponding static actuation limiters 712 may also prove advantageous in providing a means to "zero" or "home" the corresponding capstan assembly 602*d-f* in preparation for operation.

In some embodiments, an intermediary component (not shown) may interpose one or more of the capstan receptors 704*a-c*, where the static actuation limiter 712 is provided, and the corresponding cable pulley 608*d-f*, where the dynamic actuation limiter 610. In such embodiments, the intermediary component and the cable pulley 608*d-f* may be able to rotate relative to the other within a predetermined range of angular motion. In some embodiments, the predetermined range of angular motion may allow for more than 360 degrees of actuation (rotation) of the cable pulley 608*d-f*. At a specified angular location, however, the dynamic actuation limiter 610 on the cable pulley 608*d-f* may be configured to contact a first dynamic limiter on the intermediary component, and subsequently a second dynamic limiter on the intermediary component would rotate and engage the static actuation limiter 712 provided on the corresponding capstan receptor 704*a-c*.

Figure 9B:
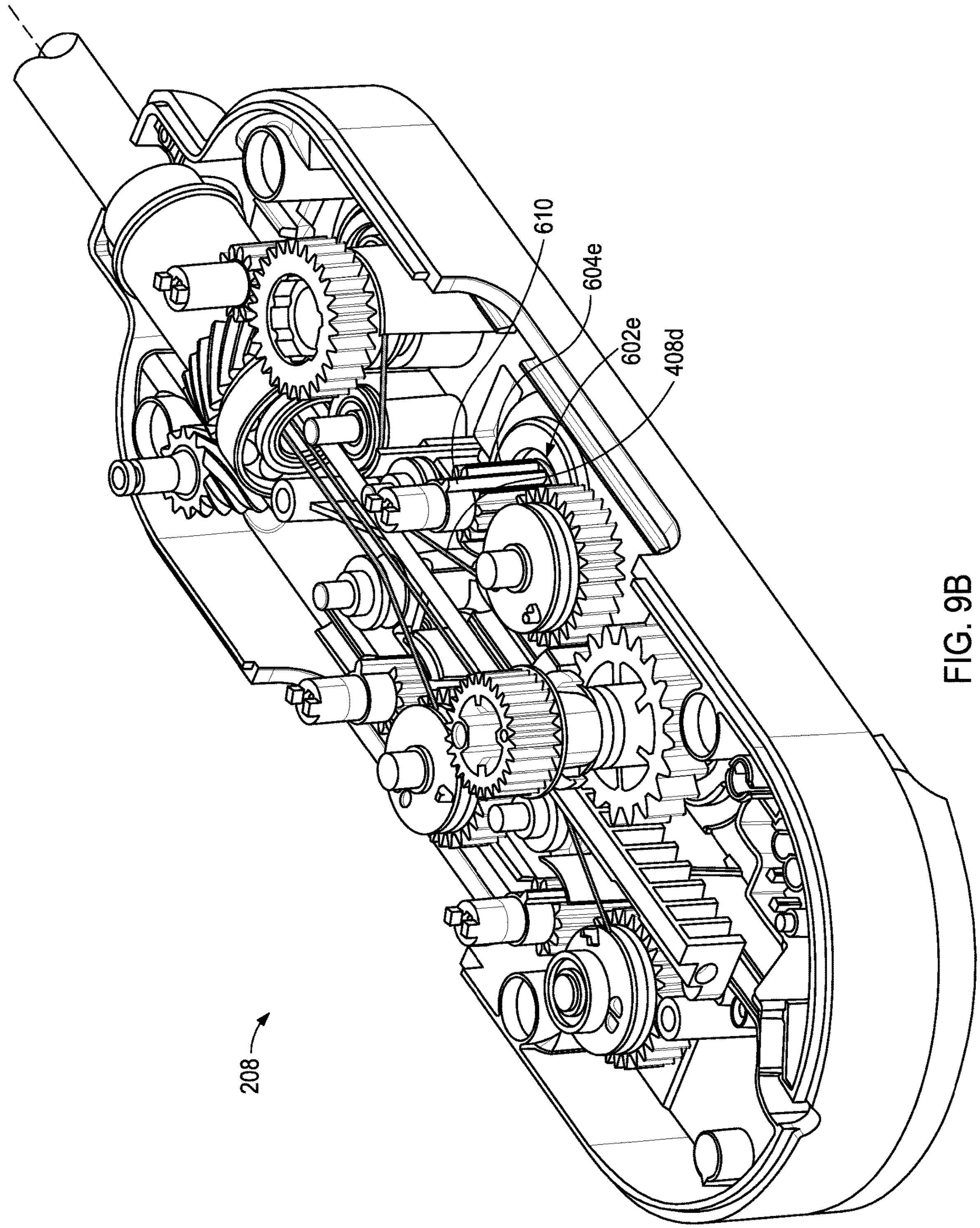
FIG. 9B is an exposed isometric view of the interior of the drive housing of FIG. 2, according to one or more additional embodiments.

FIG. 9B is an exposed isometric view of the interior of the drive housing 208, according to one or more additional embodiments. In the illustrated embodiment, the dynamic actuation limiter 610 may be provided on a drive gear of one of the capstan assemblies 602*c-f*. More specifically, as illustrated, the drive gear 604*e* of the capstan assembly 602*e* includes the dynamic actuation limiter 610, which may comprise an extended portion or extension of one of the gear teeth of the drive gear 604*e*. In other embodiments, the dynamic actuation limiter 610 may comprise a protrusion, a tab, or a boss coupled to and extending from the drive gear 604*e*.

The dynamic actuation limiter 610 may be configured and positioned to interface with a static actuation limiter (not shown) provided and otherwise defined on the drive housing 208, such as on the upper portion 702 (FIG. 7), a lower portion (not shown) of the drive housing 208, or otherwise provided by the chassis 706 (FIG. 7) that may be secured within the drive housing. In example operation, as the capstan assembly 602*e* is actuated, drive gear 604*e* is rotated, which correspondingly moves (e.g., rotates) the dynamic actuation limiter 610 provided on the drive gear 604*e*. The dynamic actuation limiter 610 is able to be moved (rotated) until engaging a corresponding static actuation limiter provided on the drive housing 208, at which point actuation of the capstan assembly 602*e* is stopped and prevented from further actuation (rotation). In some applications, the static actuation limiter may be provided at a predetermined angular location that stops the capstan assembly 602*e* from over actuation (rotation), which helps mitigate the accumulation of slack in the corresponding drive cable 408*d* and also helps prevent potential derailment of the drive cable 408*d*.

It should be noted that while the dynamic actuation limiter 610 is shown in FIG. 9B with respect to the capstan assembly 602*e*, it will be appreciated that the dynamic actuation limiter 610 may be provided on the drive gear of any of the capstan assemblies 602*c-f*, without departing from the scope of the disclosure.

Figure 10A:
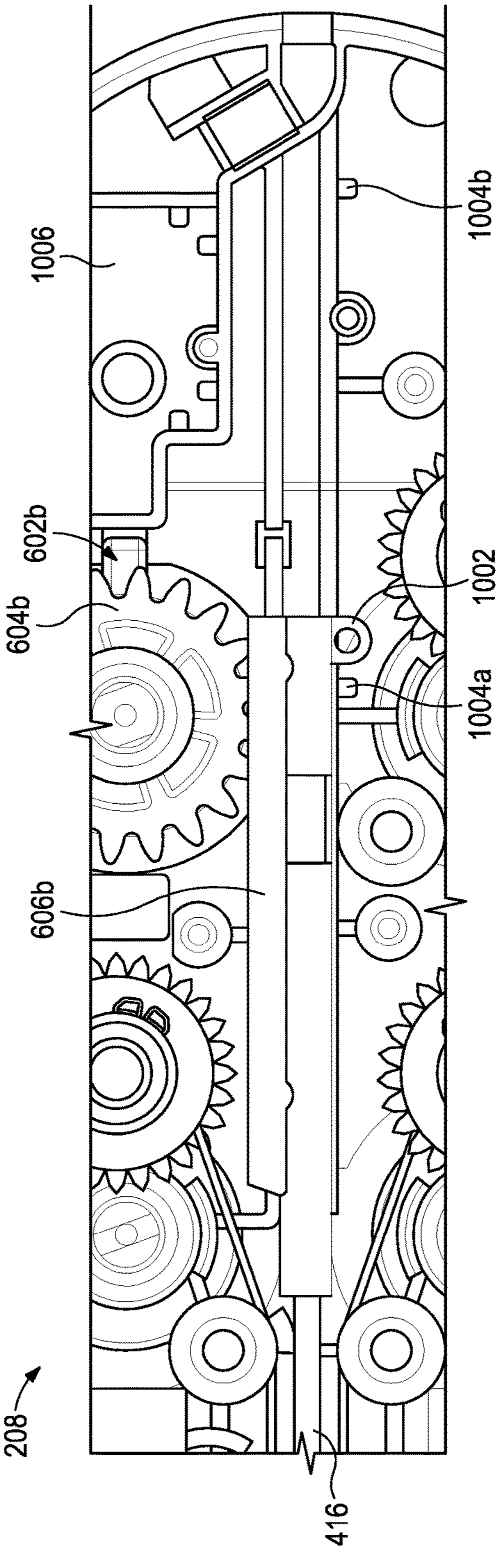
FIGS. 10A and 10B are plan views of a portion of the interior the drive housing of FIG. 2, according to one or more additional embodiments.
Figure 10B:
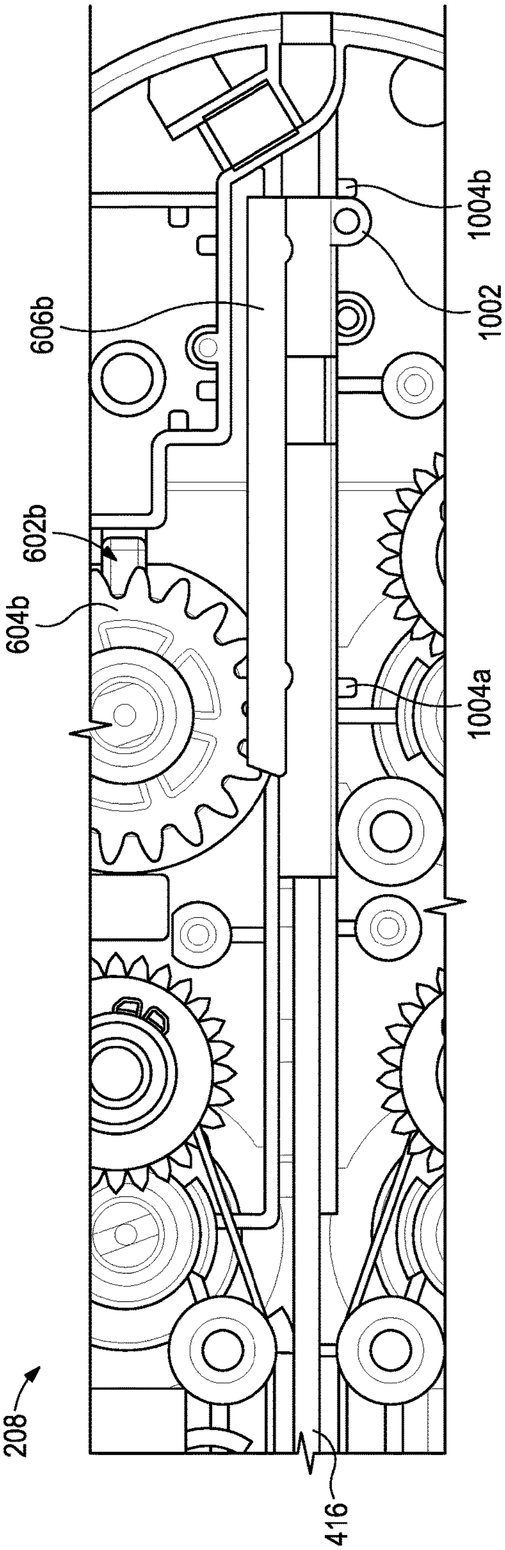

FIGS. 10A and 10B are plan views of a portion of the interior the drive housing 208, according to one or more additional embodiments. More specifically, FIGS. 10A-10B are plans view of the second capstan assembly 602*b*, which includes the drive gear 604*b* arranged to drive the driven gear 606*b* positioned within the drive housing 208. The driven gear 606*b* (e.g., a rack gear) is longitudinally translatable within the drive housing 208 when acted on by the drive gear 604*b*, and the drive rod 416 is operatively coupled to the driven gear 606*b* such that movement of the drive gear 604*b* correspondingly moves the drive rod 416 and the knife (not shown) coupled to the opposing end of the drive rod 416.

According to one or more embodiments, excessive actuation (longitudinal movement) of the driven gear 606*b* may be mitigated and otherwise entirely prevented by including a dynamic actuation limiter 1002 in the second capstan assembly 602*b*. As illustrated, the dynamic actuation limiter 1002 may comprise a tab or projection extending laterally from the driven gear 606*b*. During actuation of the second capstan assembly 602*b*, the dynamic actuation limiter 1002 may prevent the driven gear 606*b* from overextension either distally or proximally. This may prove advantageous in preventing the drive rod 416 from over extending distally and thereby resulting in the knife (not shown) from bottoming out in the guide tracks provided in the jaws 210, 212 (FIGS. 2 and 4).

As illustrated, the drive housing 208 may provide and otherwise define a first or "distal" static actuation limiter 1004*a* and a second or "proximal" static actuation limiter 1004*b*. In some embodiments, as illustrated, the static actuation limiters 1004*a,b* may be provided on the second or "lower" portion 1006 of the drive housing 208, but one or both of the static actuation limiters 1004*a,b* may be provided on the upper portion 702 (FIG. 7), without departing from the scope of the disclosure. The distal static actuation limiter 1004*a* may be arranged to stop distal movement of the driven gear 606*b* when firing the knife, and the proximal static actuation limiter 1004*b* may be arranged to stop proximal movement of the driven gear 606*b* when retracting the knife. Those skilled in the art will readily appreciate that it may be advantageous to have the driven gear 606*b* bottom out in the drive housing 208 rather than having the knife advanced too far distally within the guide tracks in the jaws 210, 212 (FIGS. 2 and 4) or retracted too far proximally.

During normal operation, the dynamic actuation limiter 1002 will typically not engage either of the static actuation limiters 1004*a,b*. However, in the event the second capstan assembly 602*b* attempts to be over actuated (or over rotated), interaction (engagement) between the dynamic actuation limiter 1002 and the static actuation limiters 1004*a,b*, in either direction, may prove advantageous in ensuring that the driven gear 606*b* is not excessively advanced or retracted. Moreover, interaction between the dynamic actuation limiter 1002 and the static actuation limiters 1004*a,b* may also prove advantageous in providing a means to "zero" or "home" the second capstan assembly 602*b-f* in preparation for operation.

Drive System Passive Cable Anti-Derailment Features

Figure 11:
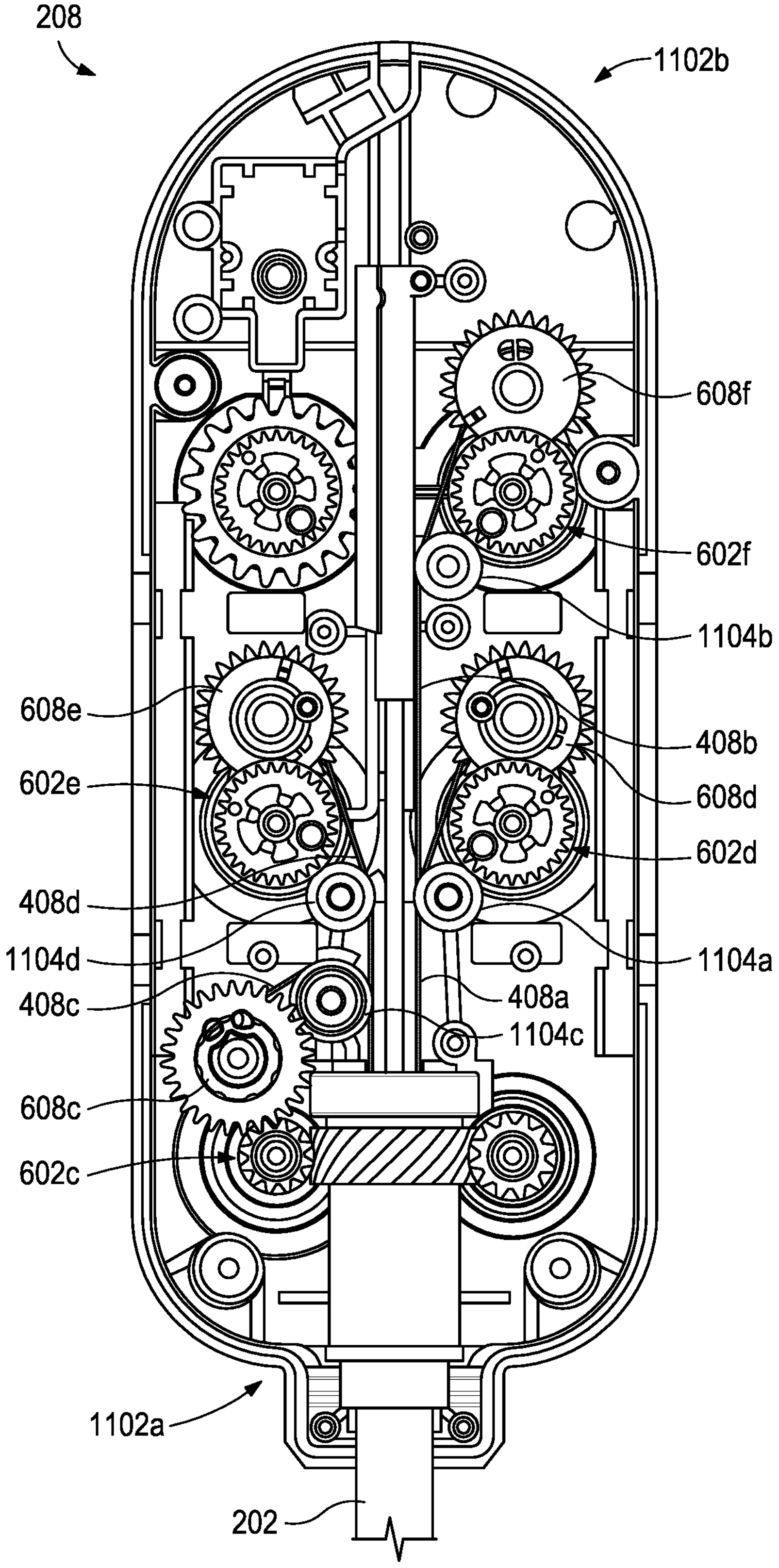
FIG. 11 is a top, exposed view of the drive housing of FIG. 2, according to one or more embodiments.

FIG. 11 is a top, exposed view of the drive housing 208, according to one or more embodiments. As illustrated, the drive housing 208 provides a first or "distal" end 1102*a* through which the shaft 202 extends, and a second or "proximal" end 1102*b* opposite the distal end 1102*a*.

In some embodiments, one or more of the drive cables 408*a-d* may engage and otherwise wrap at least partially around an idler pulley rotatably mounted within the drive housing 208. Each idler pulley may be configured to re-direct the trajectory or cable routing pathway for the corresponding drive cable 408*a-d* before the drive cable 408*a-d* is ultimately coupled to the corresponding cable pulley 608*c-f* and driven by the corresponding capstan assembly 602*c-f*. In the illustrated embodiment, the first drive cable 408*a* engages and is re-directed by a first idler pulley 1104*a*, the second drive cable 408*b* engages and is re-directed by a second idler pulley 1104*b*, the third drive cable 408*c* engages and is re-directed by a third idler pulley 1104*c*, and the fourth drive cable 408*d* engages and is re-directed by a fourth idler pulley 1104*d*. In other embodiments, however, one or more of the idler pulleys 1104*a-d* may be omitted, and the corresponding drive cable 408*a-d* may instead be received directly at the corresponding cable pulley 608.

As mentioned above, the antagonistic architecture for the drive cables 408*a-d* enables the amount of tension in each drive cable 408*a-d* to be changed, which can help accurately control operation and actuation of the end effector 204 (FIGS. 2 and 4). However, routing the drive cables 408*a-d* through or around the idler pulleys 1104*a-d* can increase the risk of accumulating slack in the drive cables 408*a-d*, which could result in the drive cables 408*a-d* derailing from the corresponding cable pulley 608*c-f* and/or the corresponding idler pulley 1104*a-d*.

According to one or more embodiments of the present disclosure, the drive housing 208 may include one or more anti-derailment features and standoffs that interface with the routing of the drive cables 408*a-d* such that the drive cables 408*a-d* are retained within the pulley grooves of the cable pulley 608*c-f* and/or the idler pulley 1104*a-d*. In event that a given drive cable 408*a-d* slackens during operation, the drive cable 408*a-d* will engage the anti-derailment feature or standoff, which helps maintain the drive cable 408*a-d* in the proper cable routing pathway until tension is resumed once more. Those skilled in the art will appreciate that the anti-derailment features and standoffs described herein are applicable to both antagonistic and closed-loop systems, which also have a tendency to slacken or creep over time.

Figure 12:
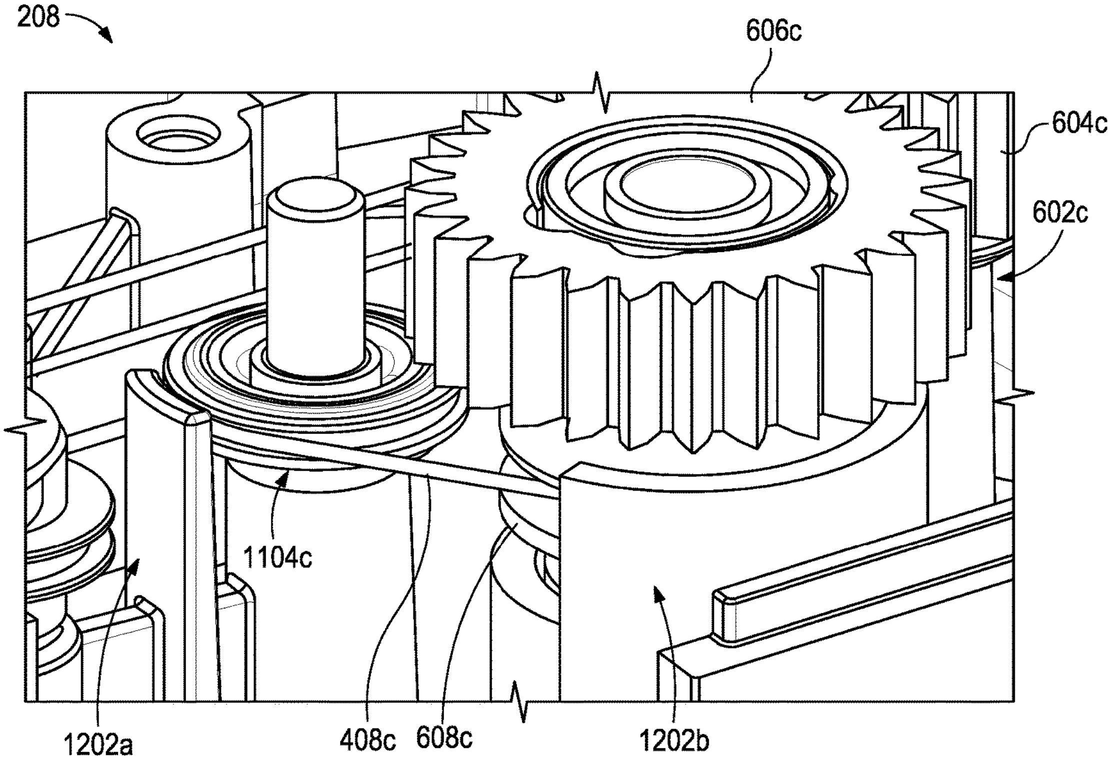
FIG. 12 is an enlarged, isometric view of a portion of the interior of the drive housing of FIG. 2, according to one or more embodiments.

FIG. 12 is an enlarged, isometric view of a portion of the interior of the drive housing 208, according to one or more embodiments. More specifically, depicted is an enlarged view of the third capstan assembly 602*c*, which includes the drive gear 604*c* (partially shown), the driven gear 606*c*, and the cable pulley 608*c* (partially occluded). The idler pulley 1104*c* is also depicted, and the third drive cable 408*c* is routed around the idler pulley 1104*c* to be received by and secured to the cable pulley 608*c*. It is noted that while the following discussion is directed to the third capstan assembly 602*c*, the principles discussed herein below are equally applicable to the other "drive cable" capstan assemblies 602*d-f* (FIGS. 6 and 11).

One or more anti-derailment features, shown as a first anti-derailment feature 1202*a* and a second anti-derailment feature 1202*b*, may be included in the drive housing 208 and configured to interface with the routing of the third drive cable 408*c*. In the illustrated embodiment, the anti-derailment features 1202*a,b* may comprise passive or static structural components extending from the drive housing 208. In some embodiments, for example, one or both of the anti-derailment features 1202*a,b* may extend from the second or "lower" portion 1006 (FIG. 10) of the drive housing 208, but could alternatively extend from the first or "upper" portion 702 (FIG. 7) of the drive housing 208. In yet other embodiments, one or both of the anti-derailment features 1202*a,b* may extend from the chassis 706 (FIG. 7) secured to the interior of the drive housing 208. In even further embodiments, one or both of the anti-derailment features 1202*a,b* may comprise component parts that are separate from the drive housing 208 and/or the chassis 706, and in such embodiments the anti-derailment feature(s) 1202*a,b* may be secured within the interior of the drive housing 208 by being captured between the upper and lower portions 702, 1006, or between the chassis 706 and a portion of the drive housing 208, without departing from the scope of the disclosure.

In some embodiments, as illustrated, one or both of the anti-derailment features 1202*a,b* may comprise arcuate structural members configured to extend about a portion of an adjacent idler pulley or cable pulley, and thereby help retain the drive cable within the idler or cable pulley during operation. More specifically, the first anti-derailment feature 1202*a* is arranged adjacent the idler pulley 1104*c*, but offset slightly from the outer circumference of the idler pulley 1104*c* to help retain the third drive cable 408*c* within the groove of the idler pulley 1104*c*. Similarly, the second anti-derailment feature 1202*b* is arranged adjacent the cable pulley 608*c*, but offset slightly from the outer circumference of the cable pulley 608*c* to help retain the third drive cable 408*c* within the groove of the cable pulley 608*c*. In event of a slack scenario, the third drive cable 408*c* will contact one or both of the anti-derailment features 1202*a,b*, which will ensure that the third drive cable 408*c* will slacken in location and resume its intended cable pathway route once tension is restored.

Figure 13:
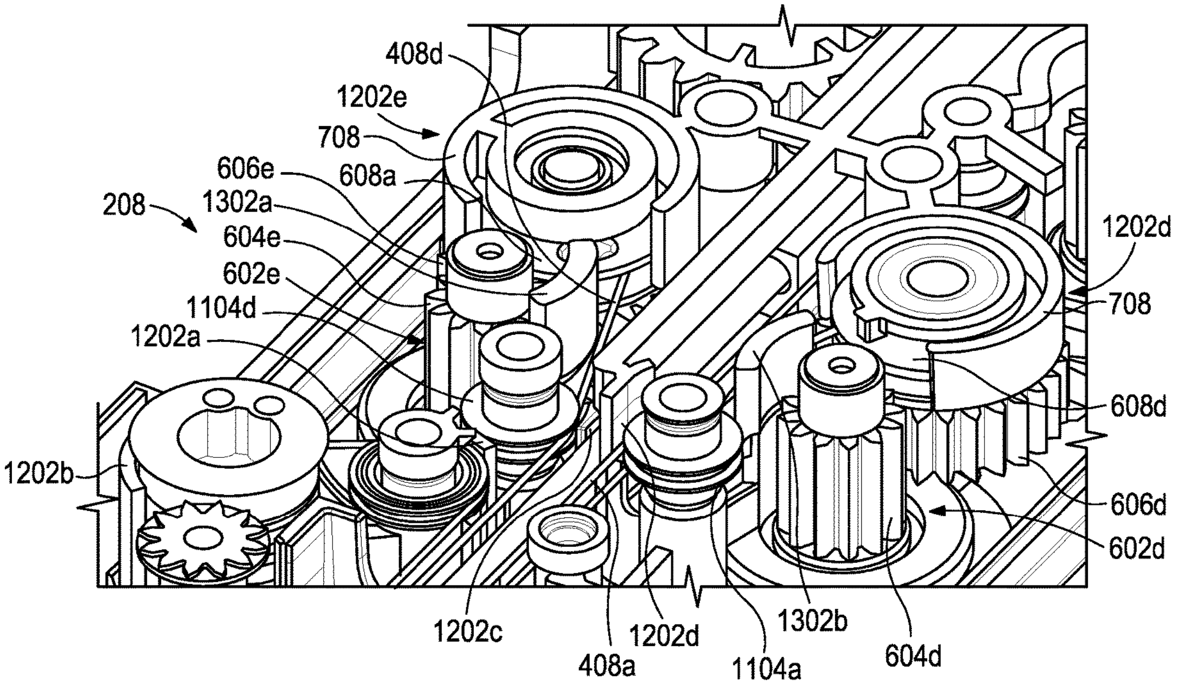
FIG. 13 is an isometric, partial cross-sectional view of a portion of the interior the drive housing of FIG. 2, according to one or more additional embodiments.

FIG. 13 is an isometric, partial cross-sectional view of a portion of the interior of the drive housing 208, according to one or more additional embodiments. More specifically, FIG. 13 depicts additional anti-derailment features, shown as a third anti-derailment feature 1202*c*, a fourth anti-derailment feature 1202*d*, a fifth anti-derailment feature 1202*e*, and a sixth anti-derailment feature 1202*f*. Similar to the anti-derailment features 1202*a,b* of FIG. 12, the anti-derailment features 1202*c-f* may comprise passive or static structural components extending from the drive housing 208, such as from the upper portion 702 (FIG. 7) of the drive housing 208, the lower portion 1006 (FIG. 10) of the drive housing 208, or from the chassis 706 (FIG. 7). Moreover, one or more of the anti-derailment features 1202*c-f* may comprise arcuate structural members configured to extend about a portion of an adjacent idler pulley or cable pulley, and thereby help retain the drive cable within the idler or cable pulley during operation In the illustrated embodiment, the third anti-derailment feature 1202*c* is arranged adjacent the idler pulley 1104*d*, but offset slightly from its outer circumference to help retain the fourth drive cable 408*d* within the groove of the idler pulley 1104*d*. Similarly, the fourth anti-derailment feature 1202*d* is arranged adjacent the idler pulley 1104*a*, but offset slightly from its outer circumference to help retain the first drive cable 408*a* within the groove of the idler pulley 1104*a*. In contrast, the fifth anti-derailment feature 1202*e* is arranged adjacent the cable pulley 608*a*, but offset slightly from its outer circumference to help retain the fourth drive cable 408*d* within the groove of the cable pulley 608*a*. Similarly, the sixth anti-derailment feature 1202*f* is arranged adjacent the cable pulley 608*d*, but offset slightly from its outer circumference to help retain the first drive cable 408*a* within the groove of the cable pulley 608*d*.

In some embodiments, the fifth and sixth anti-derailment features 1202*e,f* may comprise the outer ring 708 of the corresponding capstan receptor 704*b* and 704*a* (FIGS. 7 and 9), respectively. Accordingly, the fifth and sixth anti-derailment features 1202*e,f* may serve a dual purpose and may be provided by the chassis 706 (FIG. 7).

Standoffs for Cable Protection to Maintain Tool Operability

When a given drive cable 408*a-d* slackens and otherwise undergoes a slack event, there is a further risk that the drive cable 408*a-d* may flex and inadvertently contact features within the drive housing 208 that could damage the drive cable 408*a-d*. For instance, a slackened drive cable 408*a-d* could feed into adjacent intermeshed gears, or engage sharp or protruding features provided on actuating (dynamic) members within the drive housing 208. In such a scenario, the drive cable 408*a-d* could be irreparably damaged, which could impair or prevent further use of the surgical tool 200 (FIG. 2).

According to embodiments of the present disclosure, the drive housing 208 may include one or more standoff features that interface with the routing of the drive cables 408*a-d* such that the drive cables 408*a-d* are prevented from making contact with unintended interfaces or structures, such as adjacent intermeshed gears. In event that a given drive cable 408*a-d* slackens during operation, instead of accidentally feeding into adjacent intermeshed gears, the drive cable 408*a-d* will engage the standoff feature until tension is resumed once more. Those skilled in the art will appreciate that the standoff features described herein are applicable to both antagonistic and closed-loop systems, which also have a tendency to slacken or creep over time.

Still referring to FIG. 13, one or more standoff features, shown as a first standoff feature 1302*a* and a second standoff feature 1302*b*, may be included in the drive housing 208 and configured to interface with the routing of the fourth and second drive cables 408*d,b*, respectively. The standoff features 1302*a,b* may comprise passive or static structural components extending from the drive housing 208. In some embodiments, for example, one or both of the standoff features 1302*a,b* may extend from the upper portion 702 (FIG. 7) of the drive housing 208, but could alternatively extend from the lower portion 1006 (FIG. 10) of the drive housing 208. In other embodiments, one or both of the standoff features 1302*a,b* may form part of or extend from the chassis 706 (FIG. 7) secured to the interior of the drive housing 208. In yet other embodiments, one or both of the standoff features 1302*a,b* may extend from a combination of the upper and lower portions 702, 1006 and/or the chassis 706, without departing from the scope of the disclosure.

In some embodiments, as illustrated, one or both of the standoff features 1302*a,b* may comprise arcuate structural members, but could alternatively comprise straight structural features. More specifically, the first standoff feature 1302*a* is arranged at the fifth capstan assembly 602*e* and interposing the fourth drive cable 408*d* and at least a portion of the geared interface between the drive gear 604*e* and the driven gear 606*e*. In event of a slack scenario, the fourth drive cable 408*d* will contact the first standoff feature 1302*a*, which will ensure that the fourth drive cable 408*d* is not inadvertently fed into the geared interface between the drive gear 604*e* and the driven gear 606*e*.

Similarly, the second standoff feature 1302*b* is arranged at the fourth capstan assembly 602*d* and interposing the first drive cable 408*a* and at least a portion of the geared interface between the drive gear 604*d* and the driven gear 606*d*. In event of a slack scenario, the first drive cable 408*a* will contact the second standoff feature 1302*b*, which will ensure that the first drive cable 408*a* is not inadvertently fed into the geared interface between the drive gear 604*d* and the driven gear 606*d*.

Figure 14:
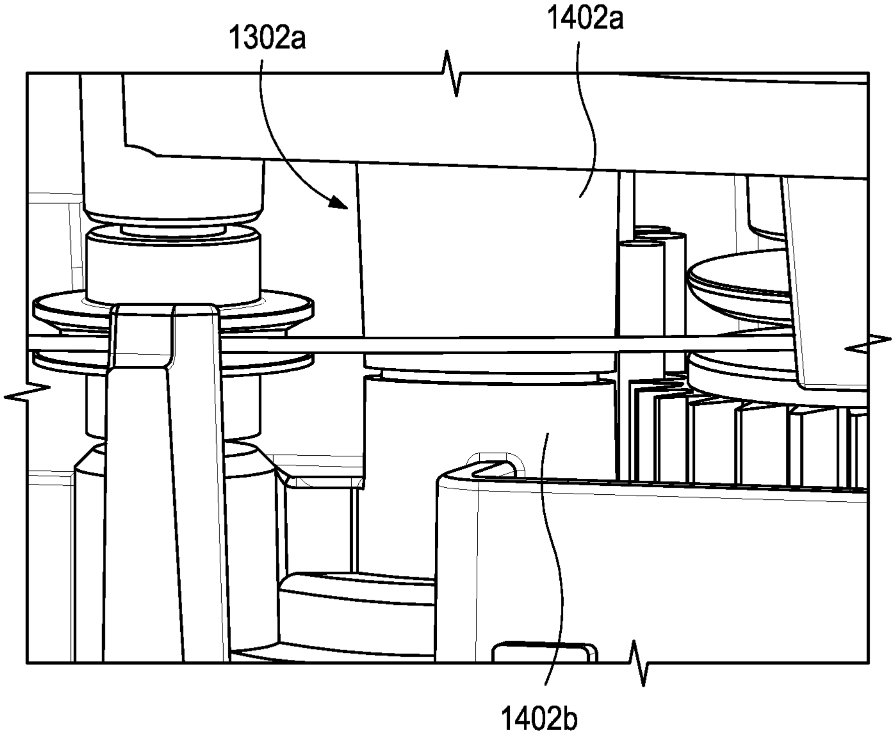
FIG. 14 is an enlarged view of the first standoff feature of FIG. 13, according to one or more embodiments.

FIG. 14 is an enlarged view of the first standoff feature 1302*a*, according to one or more embodiments. While the following discussion is related to the first standoff feature 1302*a*, it is equally applicable to the second standoff feature 1302*b* (FIG. 13).

In some embodiments, as illustrated, the first standoff feature 1302 may comprise multiple component parts, shown as a first or “upper” member 1402*a* and a second or “lower” member 1402*b*. The upper member 1402*a* may extend from an upper portion of the drive housing 208, such as the upper portion 702 (FIG. 7) or the chassis 706 (FIG. 7) secured to the upper portion 702, and the lower member 1402*b* may extend from the lower portion 1006 (FIG. 10) of the drive housing 208. When the upper and lower portions 702, 1006 of the drive housing 208 are mated, the upper and lower members 1402*a,b* may be configured to align vertically and meet at a horizontal interface. In such embodiments, the upper and lower members 1402*a,b* may operate to help locate and align the upper and lower portions 702, 1006 of the drive housing 208 for a proper mated engagement.

In other embodiments, the first standoff feature 1302*a* (or any of the standoff features described herein) may comprise a component part that is separate from the drive housing 208 and/or the chassis 706 (FIG. 7). In such embodiments, the first standoff feature 1302*a* may be secured within the interior of the drive housing 208 by being captured between the upper and lower portions 702 (FIG. 7), 1006 (FIG. 10), or between the chassis 706 and a portion of the drive housing 208, without departing from the scope of the scope of the disclosure.

Combination Members Maintaining Cable Routing

Figure 15:
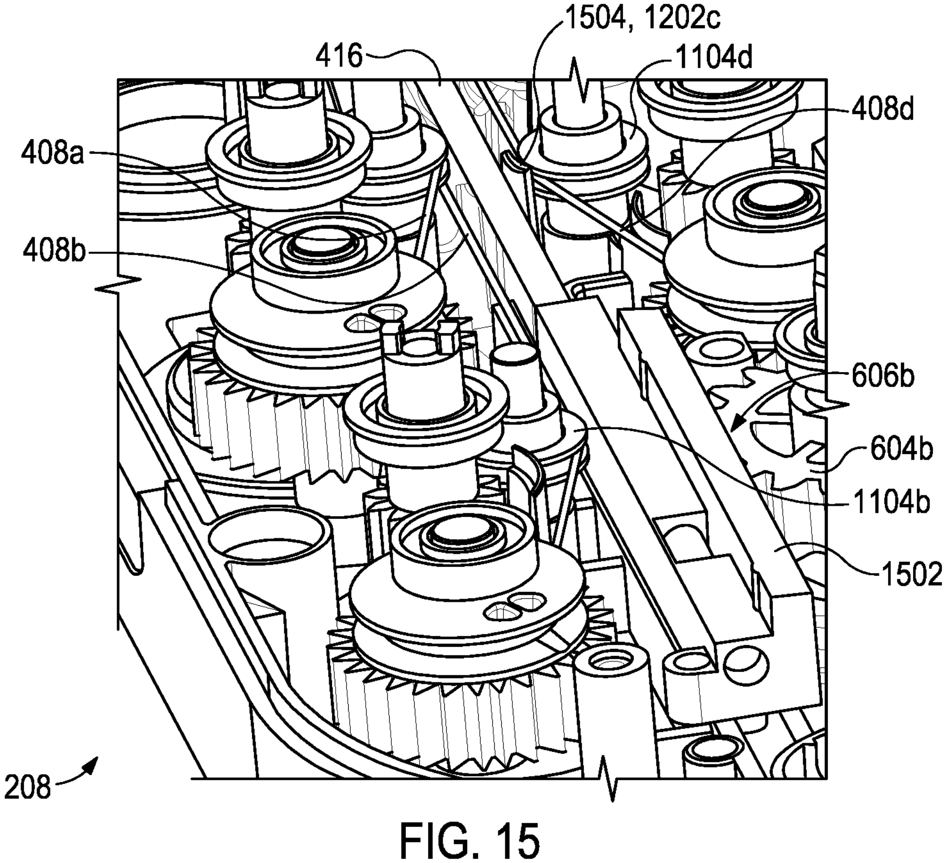
FIG. 15 is an enlarged, exposed view of a portion of the drive housing FIG. 2, according to one or more additional embodiments.

FIG. 15 is an enlarged, exposed view of a portion of the drive housing 208, according to one or more additional embodiments. According to embodiments of the present disclosure, the drive housing 208 may further house and otherwise include one or more active or dynamic anti-derailment features. Dynamic anti-derailment features may prove advantageous in some surgical tools where the footprint within the drive housing 208 is very space constrained with multiple systems. The dynamic anti-derailment features provide anti-derailment protection in a region where a passive/static structural component is difficult to accommodate.

In one or more embodiments, the driven gear or “rack gear” 606*b* may have a dual function and operate as a dynamic anti-derailment feature 1502 for at least the second drive cable 408*b*. As described herein, the rack gear 606*b* may be driven in longitudinal translation by operation of the drive gear 604*b*, and longitudinally moving the rack gear 606*b* will correspondingly move the drive rod 416 in the same longitudinal direction, which results in a knife (not shown) coupled to the end of the drive rod 416 moving in the same longitudinal direction. However, the rack gear 606*b* may also operate and comprise a dynamic anti-derailment feature 1502.

As illustrated, the dynamic anti-derailment feature 1502 (e.g., the rack gear 606*b*) provides an elongate body positioned laterally adjacent the idler pulley 1104*b*, which is arranged to engage and re-direct the second drive cable 408*b*. In event that the second drive cable 408*b* slackens during operation, the second drive cable 408*b* will engage the active anti-derailment feature 1502 (i.e., the side of the rack gear 606*b*), which helps maintain the second drive cable 408*b* within the groove of the idler pulley 1104*b* until tension is resumed once more.

Since the dynamic anti-derailment feature 1502 has an elongate body, the active anti-derailment feature 1502 is able to prevent the second drive cable 408*b* from migrating out of the groove of the idler pulley 1104*b* even when the rack gear 606*b* is longitudinally moved. Accordingly, the active anti-derailment feature 1502 is able to maintain proper routing of the second drive cable 408*b* in any functional actuated state (e.g., longitudinal position).

In some embodiments, the drive housing 208 may further include one or more additional standoff features 1504. In at least one embodiment, the standoff feature 1504 may comprise the same structure as the third anti-derailment feature 1202*c*, which is arranged adjacent the idler pulley 1104*d* to help retain the fourth drive cable 408*d* within the groove of the idler pulley 1104*d*. The standoff feature 1504, however, may also be arranged and otherwise configured to guide and support the drive rod 416 as the rack gear 606*b* and the drive rod 416 are longitudinally translated. The standoff feature 1504 may comprise a passive or static structural component extending from the drive housing 208, such as from the lower portion 1006 (FIG. 10) of the drive housing 208, but could alternatively extend from the upper portion 702 (FIG. 7) or from the chassis 706 (FIG. 7). In other embodiments, however, the standoff feature 1504 may comprise a component part that is separate from the drive housing 208 and/or the chassis 706. In such embodiments, the standoff feature 1504 may be secured within the interior of the drive housing 208 by being captured between the upper and lower portions 702 (FIG. 7), 1006 (FIG. 10), or between the chassis 706 and a portion of the drive housing 208, without departing from the scope of the disclosure.

Embodiments disclosed herein include:

A. A surgical tool includes a drive housing, a drive input rotatably mounted to a bottom of the drive housing, a capstan assembly arranged within the drive housing and operatively coupled to the drive input such that rotation of the drive input correspondingly actuates the capstan assembly, a static actuation limiter arranged within the drive housing, and a dynamic actuation limiter provided by the capstan assembly and engageable with the static actuation limiter as the capstan assembly is actuated, wherein engaging the dynamic actuation limiter against the static actuation limiter stops actuation of the capstan assembly.

B. A method of operating a surgical tool includes positioning the surgical tool adjacent a patient for operation, the surgical tool including a drive housing, a drive input rotatably mounted to a bottom of the drive housing, a capstan assembly arranged within the drive housing and operatively coupled to the drive input, a static actuation limiter arranged within the drive housing, and a dynamic actuation limiter provided by the capstan assembly. The method further includes rotating the drive input and thereby actuating the capstan assembly, engaging the dynamic actuation limiter against the static actuation limiter as the capstan assembly is actuated, and stopping actuation of the capstan assembly when the dynamic actuation limiter engages the static actuation limiter.

C. A surgical tool includes a drive housing, a drive input rotatably mounted to a bottom of the drive housing, a capstan assembly arranged within the drive housing and operatively coupled to the drive input such that rotation of the drive input correspondingly actuates the capstan assembly, the capstan assembly including a cable pulley, and a drive cable operatively coupled to the cable pulley and extending from the capstan assembly. The surgical tool further includes an anti-derailment feature offset from an outer circumference of the cable pulley and operable to maintain the drive cable within the cable pulley as the cable pulley rotates.

D. A surgical tool that includes a drive housing, a drive input rotatably mounted to a bottom of the drive housing, a capstan assembly arranged within the drive housing and operatively coupled to the drive input such that rotation of the drive input correspondingly actuates the capstan assembly, the capstan assembly including a drive gear coupled to the drive input such that rotation of the drive input correspondingly rotates the drive gear, a driven gear positioned to intermesh with the drive gear such that rotating the drive gear correspondingly rotates the driven gear, a cable pulley forming part of the driven gear, and a drive cable operatively coupled to the cable pulley and extending from the capstan assembly. The surgical tool further including a standoff feature interposing the drive cable and a geared interface between the drive gear and the driven gear to prevent the drive cable from feeding into the geared interface.

Each of embodiments A, B, C, and D may have one or more of the following additional elements in any combination: Element 1: wherein the capstan assembly includes a drive gear coupled to the drive input such that rotation of the drive input correspondingly rotates the drive gear, and a driven gear positioned to intermesh with the drive gear such that rotating the drive gear correspondingly rotates the driven gear, wherein the dynamic actuation limiter is provided on the driven gear. Element 2: wherein the capstan assembly further includes a cable pulley forming part of the driven gear, and a drive cable operatively coupled to the cable pulley and extending from the capstan assembly, wherein the dynamic actuation limiter is provided on the cable pulley, and wherein engaging the dynamic actuation limiter against the static actuation limiter further prevents accumulation of slack in the drive cable. Element 3: wherein the static actuation limiter is provided at a predetermined angular location relative to the dynamic actuation limiter, and wherein the predetermined angular location is located such that a minimum angular magnitude of at least 15° of the drive cable remains wrapped about the cable pulley. Element 4: wherein the capstan assembly includes a drive gear coupled to the drive input such that rotation of the drive input correspondingly rotates the drive gear, and a driven gear positioned to intermesh with the drive gear such that rotating the drive gear correspondingly rotates the driven gear, wherein the dynamic actuation limiter is provided on the drive gear. Element 5: further comprising a capstan receptor arranged within the drive housing and including an outer ring sized to receive and extend about an outer circumference of a cable pulley of the capstan assembly, and an inner ring concentrically arranged within the outer ring and sized to receive and extend about a bearing rotatably mounted to the cable pulley, wherein the static actuation limiter extends from at least one of the outer and inner rings. Element 6: wherein the capstan receptor is provided on a chassis secured within the drive housing. Element 7:

wherein the capstan assembly includes a drive gear coupled to the drive input such that rotation of the drive input correspondingly rotates the drive gear, and a rack gear positioned to intermesh with the drive gear such that rotating the drive gear correspondingly translates the rack gear longitudinally within the drive housing, wherein the dynamic actuation limiter is provided on the rack gear. Element 8: wherein the static actuation limiter comprises a distal static actuation limiter, and a proximal static actuation limiter, and wherein the dynamic actuation limiter is engageable with the distal and static actuation limiters to stop distal and proximal longitudinal movement of the rack gear. Element 9: wherein the capstan assembly includes a cable pulley, a drive cable operatively coupled to the cable pulley and extending from the capstan assembly, and an anti-derailment feature offset from an outer circumference of the cable pulley and operable to maintain the drive cable within the cable pulley as the cable pulley rotates. Element 10: wherein the anti-derailment feature comprises a first anti-derailment feature, and the capstan assembly further includes an idler pulley that receives and re-directs the drive cable, and a second anti-derailment feature offset from an outer circumference of the idler pulley and operable to maintain the drive cable within the idler pulley. Element 11: wherein the capstan assembly includes a drive gear coupled to the drive input such that rotation of the drive input correspondingly rotates the drive gear, a driven gear positioned to intermesh with the drive gear such that rotating the drive gear correspondingly rotates the driven gear, a cable pulley forming part of the driven gear, a drive cable operatively coupled to the cable pulley and extending from the capstan assembly, and a standoff feature interposing the drive cable and a geared interface between the drive gear and the driven gear to prevent the drive cable from feeding into the geared interface. Element 12: wherein the standoff feature comprises an upper member extend from an upper portion of the drive housing or a chassis arranged within the upper portion, and a lower member extending from a lower portion of the drive housing and aligned vertically with the upper member when the upper portion is mated to the lower portion. Element 13: further comprising a pulley rotatably mounted within the drive housing, a drive cable at least partially wrapped around the pulley, a rack gear arranged within the drive housing adjacent the pulley and positioned to intermesh with a drive gear such that rotating the drive gear correspondingly translates the rack gear longitudinally within the drive housing, wherein the rack gear operates as a dynamic anti-derailment feature that maintains the drive cable at least partially wrapped around the pulley as the rack gear longitudinally translates. Element 14: further comprising a drive rod operatively coupled to the rack gear such that translation of the rack gear correspondingly moves the drive rod in a same longitudinal direction, and a standoff feature arranged within the drive housing to guide and support the drive rod as the rack gear and the drive rod are longitudinally translated.

Element 15: wherein the capstan assembly includes a cable pulley and a drive cable operatively coupled to the cable pulley, the dynamic actuation limiter being provided on the cable pulley, and wherein engaging the dynamic actuation limiter against the static actuation limiter comprises stopping rotation of cable pulley when the dynamic actuation limiter engages the static actuation limiter, and preventing an accumulation of slack in the drive cable once the cable pulley stops rotation. Element 16: further comprising maintaining at least 15° of the drive cable wrapped about the cable pulley when rotation of the cable pulley is stopped. Element 17: wherein the static actuation limiter includes a distal static actuation limiter and a proximal static actuation limiter, and the capstan assembly includes a drive gear coupled to the drive input, and a rack gear positioned to intermesh with the drive gear, the method further comprising rotating the drive input and thereby rotating the drive gear, translating the rack gear longitudinally within the drive housing as the drive gear as the drive gear rotates, engaging one of the distal and proximal static actuation limiters with the dynamic actuation limiter, and homing the capstan assembly as the dynamic actuation limiter engages the one of the distal and proximal static actuation limiters. Element 18: wherein the capstan assembly includes a cable pulley, and a drive cable operatively coupled to the cable pulley and extending from the capstan assembly, the method further comprising maintaining the drive cable within the cable pulley as the cable pulley rotates with an anti-derailment feature offset from an outer circumference of the cable pulley. Element 19: wherein the anti-derailment feature comprises a first anti-derailment feature, and the capstan assembly further includes an idler pulley that receives and re-directs the drive cable, the method further comprising maintaining the drive cable within the idler pulley with a second anti-derailment feature offset from an outer circumference of the idler pulley. Element 20: wherein the capstan assembly includes a drive gear, a driven gear positioned to intermesh with the drive gear, a cable pulley forming part of the driven gear, and a drive cable operatively coupled to the cable pulley and extending from the capstan assembly, the method further comprising preventing the drive cable from feeding into a geared interface between the drive gear and the driven gear with a standoff feature interposing the drive cable and the geared interface.

Element 21: wherein the anti-derailment feature comprises a first anti-derailment feature, and the capstan assembly further includes an idler pulley that receives and re-directs the drive cable, and a second anti-derailment feature offset from an outer circumference of the idler pulley and operable to maintain the drive cable within the idler pulley. Element 22: wherein the drive cable is a first drive cable, the surgical tool further comprising a pulley rotatably mounted within the drive housing, a second drive cable at least partially wrapped around the pulley, a rack gear arranged within the drive housing adjacent the pulley and positioned to intermesh with a drive gear such that rotating the drive gear correspondingly translates the rack gear longitudinally within the drive housing, wherein the rack gear operates as a dynamic anti-derailment feature that maintains the second drive cable at least partially wrapped around the pulley as the rack gear longitudinally translates.

Element 23: wherein the standoff feature comprises an upper member extend from an upper portion of the drive housing or a chassis arranged within the upper portion, and a lower member extending from a lower portion of the drive housing and aligned vertically with the upper member when the upper portion is mated to the lower portion.

By way of non-limiting example, exemplary combinations applicable to A, B, C, and D include: Element 1 with Element 2; Element 2 with Element 3; Element 5 with Element 6; Element 7 with Element 8; Element 9 with Element 10; Element 11 with Element 12; Element 13 with Element 14; Element 15 with Element 16; and Element 18 with Element 19.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A surgical tool, comprising:

a drive housing;

a drive input rotatably mounted to a bottom of the drive housing;

a capstan assembly arranged within the drive housing and operatively coupled to the drive input such that rotation of the drive input correspondingly actuates the capstan assembly;

a static actuation limiter arranged within the drive housing; and a dynamic actuation limiter provided by the capstan assembly and engageable with the static actuation limiter as the capstan assembly is actuated, wherein engaging the dynamic actuation limiter against the static actuation limiter stops actuation of the capstan assembly.

2. The surgical tool of claim 1, wherein the capstan assembly includes:

a drive gear coupled to the drive input such that rotation of the drive input correspondingly rotates the drive gear; and a driven gear positioned to intermesh with the drive gear such that rotating the drive gear correspondingly rotates the driven gear, wherein the dynamic actuation limiter is provided on the driven gear.

3. The surgical tool of claim 2, wherein the capstan assembly further includes:

a cable pulley forming part of the driven gear; and a drive cable operatively coupled to the cable pulley and extending from the capstan assembly, wherein the dynamic actuation limiter is provided on the cable pulley, and wherein engaging the dynamic actuation limiter against the static actuation limiter further prevents accumulation of slack in the drive cable.

4. The surgical tool of claim 3, wherein the static actuation limiter is provided at a predetermined angular location relative to the dynamic actuation limiter, and wherein the predetermined angular location is located such that a minimum angular magnitude of at least 15° of the drive cable remains wrapped about the cable pulley.

5. The surgical tool of claim 1, wherein the capstan assembly includes:

a drive gear coupled to the drive input such that rotation of the drive input correspondingly rotates the drive gear; and a driven gear positioned to intermesh with the drive gear such that rotating the drive gear correspondingly rotates the driven gear, wherein the dynamic actuation limiter is provided on the drive gear.

6. The surgical tool of claim 1, further comprising a capstan receptor arranged within the drive housing and including:

an outer ring sized to receive and extend about an outer circumference of a cable pulley of the capstan assembly; and an inner ring concentrically arranged within the outer ring and sized to receive and extend about a bearing rotatably mounted to the cable pulley, wherein the static actuation limiter extends from at least one of the outer and inner rings.

7. The surgical tool of claim 6, wherein the capstan receptor is provided on a chassis secured within the drive housing.

8. The surgical tool of claim 1, wherein the capstan assembly includes:

a drive gear coupled to the drive input such that rotation of the drive input correspondingly rotates the drive gear; and a rack gear positioned to intermesh with the drive gear such that rotating the drive gear correspondingly translates the rack gear longitudinally within the drive housing, wherein the dynamic actuation limiter is provided on the rack gear.

9. The surgical tool of claim 8, wherein the static actuation limiter comprises:

a distal static actuation limiter; and a proximal static actuation limiter, and wherein the dynamic actuation limiter is engageable with the distal and static actuation limiters to stop distal and proximal longitudinal movement of the rack gear.

10. The surgical tool of claim 1, wherein the capstan assembly includes:

a cable pulley;

a drive cable operatively coupled to the cable pulley and extending from the capstan assembly; and an anti-derailment feature offset from an outer circumference of the cable pulley and operable to maintain the drive cable within the cable pulley as the cable pulley rotates.

11. The surgical tool of claim 10, wherein the anti-derailment feature comprises a first anti-derailment feature, and the capstan assembly further includes:

an idler pulley that receives and re-directs the drive cable; and a second anti-derailment feature offset from an outer circumference of the idler pulley and operable to maintain the drive cable within the idler pulley.

12. The surgical tool of claim 1, wherein the capstan assembly includes:

a drive gear coupled to the drive input such that rotation of the drive input correspondingly rotates the drive gear;

a driven gear positioned to intermesh with the drive gear such that rotating the drive gear correspondingly rotates the driven gear;

a cable pulley forming part of the driven gear;

a drive cable operatively coupled to the cable pulley and extending from the capstan assembly; and a standoff feature interposing the drive cable and a geared interface between the drive gear and the driven gear to prevent the drive cable from feeding into the geared interface.

13. The surgical tool of claim 12, wherein the standoff feature comprises:

an upper member extend from an upper portion of the drive housing or a chassis arranged within the upper portion; and a lower member extending from a lower portion of the drive housing and aligned vertically with the upper member when the upper portion is mated to the lower portion.

14. The surgical tool of claim 1, further comprising:

a pulley rotatably mounted within the drive housing;

a drive cable at least partially wrapped around the pulley;

a rack gear arranged within the drive housing adjacent the pulley and positioned to intermesh with a drive gear such that rotating the drive gear correspondingly translates the rack gear longitudinally within the drive housing, wherein the rack gear operates as a dynamic anti-derailment feature that maintains the drive cable at least partially wrapped around the pulley as the rack gear longitudinally translates.

15. The surgical tool of claim 14, further comprising:

a drive rod operatively coupled to the rack gear such that translation of the rack gear correspondingly moves the drive rod in a same longitudinal direction; and a standoff feature arranged within the drive housing to guide and support the drive rod as the rack gear and the drive rod are longitudinally translated.

16. A method of operating a surgical tool, comprising:

positioning the surgical tool adjacent a patient for operation, the surgical tool including:

a drive housing;

a drive input rotatably mounted to a bottom of the drive housing;

a capstan assembly arranged within the drive housing and operatively coupled to the drive input;

a static actuation limiter arranged within the drive housing; and a dynamic actuation limiter provided by the capstan assembly;

rotating the drive input and thereby actuating the capstan assembly;

engaging the dynamic actuation limiter against the static actuation limiter as the capstan assembly is actuated; and stopping actuation of the capstan assembly when the dynamic actuation limiter engages the static actuation limiter.

17. The method of claim 16, wherein the capstan assembly includes a cable pulley and a drive cable operatively coupled to the cable pulley, the dynamic actuation limiter being provided on the cable pulley, and wherein engaging the dynamic actuation limiter against the static actuation limiter comprises:

stopping rotation of cable pulley when the dynamic actuation limiter engages the static actuation limiter; and preventing an accumulation of slack in the drive cable once the cable pulley stops rotation.

18. The method of claim 17, further comprising maintaining at least 15° of the drive cable wrapped about the cable pulley when rotation of the cable pulley is stopped.

19. The method of claim 16, wherein the static actuation limiter includes a distal static actuation limiter and a proximal static actuation limiter, and the capstan assembly includes a drive gear coupled to the drive input, and a rack gear positioned to intermesh with the drive gear, the method further comprising:

rotating the drive input and thereby rotating the drive gear;

translating the rack gear longitudinally within the drive housing as the drive gear as the drive gear rotates;

engaging one of the distal and proximal static actuation limiters with the dynamic actuation limiter; and homing the capstan assembly as the dynamic actuation limiter engages the one of the distal and proximal static actuation limiters.

20. The method of claim 16, wherein the capstan assembly includes a cable pulley, and a drive cable operatively coupled to the cable pulley and extending from the capstan assembly, the method further comprising:

maintaining the drive cable within the cable pulley as the cable pulley rotates with an anti-derailment feature offset from an outer circumference of the cable pulley.

21. The method of claim 20, wherein the anti-derailment feature comprises a first anti-derailment feature, and the capstan assembly further includes an idler pulley that receives and re-directs the drive cable, the method further comprising:

maintaining the drive cable within the idler pulley with a second anti-derailment feature offset from an outer circumference of the idler pulley.

22. The method of claim 16, wherein the capstan assembly includes a drive gear, a driven gear positioned to intermesh with the drive gear, a cable pulley forming part of the driven gear, and a drive cable operatively coupled to the cable pulley and extending from the capstan assembly, the method further comprising:

preventing the drive cable from feeding into a geared interface between the drive gear and the driven gear with a standoff feature interposing the drive cable and the geared interface.

23. A surgical tool, comprising:
a drive housing;
a drive input rotatably mounted to a bottom of the drive housing;
a capstan assembly arranged within the drive housing and operatively coupled to the drive input such that rotation of the drive input correspondingly actuates the capstan assembly, the capstan assembly including:
a cable pulley; and
a drive cable operatively coupled to the cable pulley and extending from the capstan assembly; and
an anti-derailment feature offset from an outer circumference of the cable pulley and operable to maintain the drive cable within the cable pulley as the cable pulley rotates,
wherein the anti-derailment feature comprises a first anti-derailment feature, and the capstan assembly further includes:
an idler pulley that receives and re-directs the drive cable; and
a second anti-derailment feature offset from an outer circumference of the idler pulley and operable to maintain the drive cable within the idler pulley.

24. The surgical tool of claim 23, wherein the drive cable is a first drive cable, the surgical tool further comprising:
a pulley rotatably mounted within the drive housing;
a second drive cable at least partially wrapped around the pulley; and
a rack gear arranged within the drive housing adjacent the pulley and positioned to intermesh with a drive gear such that rotating the drive gear correspondingly translates the rack gear longitudinally within the drive housing,
wherein the rack gear operates as a dynamic anti-derailment feature that maintains the second drive cable at least partially wrapped around the pulley as the rack gear longitudinally translates.

25. A surgical tool, comprising:
a drive housing;
a drive input rotatably mounted to a bottom of the drive housing;
a capstan assembly arranged within the drive housing and operatively coupled to the drive input such that rotation of the drive input correspondingly actuates the capstan assembly, the capstan assembly including:
a drive gear coupled to the drive input such that rotation of the drive input correspondingly rotates the drive gear;
a driven gear positioned to intermesh with the drive gear such that rotating the drive gear correspondingly rotates the driven gear;
a cable pulley forming part of the driven gear; and
a drive cable operatively coupled to the cable pulley and extending from the capstan assembly; and
a standoff feature interposing the drive cable and a geared interface between the drive gear and the driven gear to prevent the drive cable from feeding into the geared interface.

26. The surgical tool of claim 25, wherein the standoff feature comprises:
an upper member extend from an upper portion of the drive housing or a chassis arranged within the upper portion; and
a lower member extending from a lower portion of the drive housing and aligned vertically with the upper member when the upper portion is mated to the lower portion.

* * * * *